US012766292B2

(12) United States Patent
Maggio et al.

(10) Patent No.: US 12,766,292 B2
(45) Date of Patent: Oct. 20, 2026

(54) MICROCATHETER DEVICE WITH NON-LINEAR BENDING STIFFNESS

(71) Applicant: SCIENTIA VASCULAR, INC., West Valley City, UT (US)

(72) Inventors: Richard F. Maggio, Park City, UT (US); Edward J. Snyder, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 781 days.

(21) Appl. No.: 17/901,821

(22) Filed: Sep. 1, 2022

(65) Prior Publication Data

US 2023/0071512 A1 Mar. 9, 2023

Related U.S. Application Data

(60) Provisional application No. 63/271,114, filed on Oct. 22, 2021, provisional application No. 63/240,845, filed on Sep. 3, 2021.

(51) Int. Cl.
*A61M 25/00* (2006.01)

(52) U.S. Cl.
CPC .... *A61M 25/0054* (2013.01); *A61M 25/0023* (2013.01); *A61M 25/008* (2013.01); *A61M 2025/0042* (2013.01)

(58) Field of Classification Search
CPC .......... A61M 25/0054; A61M 25/0023; A61M 25/008; A61M 2025/0042; A61M 25/0045; A61M 25/0053; A61M 2025/0059; A61M 25/0051; A61M 25/0013
See application file for complete search history.

(56) References Cited

U.S. PATENT DOCUMENTS

| | | | |
|---|---|---|---|
| 2,022,065 | A | 11/1935 | Wappler |
| 2,187,299 | A | 1/1940 | Burkhardt |
| 3,183,702 | A | 5/1965 | Zittell |
| 3,572,334 | A | 3/1971 | Petterson |
| 3,612,058 | A | 10/1971 | Ackerman |
| 3,709,271 | A | 1/1973 | Flory |
| 3,920,058 | A | 11/1975 | Walker |

(Continued)

FOREIGN PATENT DOCUMENTS

| | | | |
|---|---|---|---|
| AU | 07230/40 | B2 | 8/2000 |
| AU | 733966 | B2 | 5/2001 |

(Continued)

OTHER PUBLICATIONS

Final Office Action received for U.S. Appl. No. 12/753,831, mailed on May 31, 2012.

(Continued)

*Primary Examiner* — Cris L. Rodriguez
(74) *Attorney, Agent, or Firm* — Workman Nydegger

(57) ABSTRACT

Disclosed are microcatheter devices with features that provide effective axial response, good distribution of bending forces, and a smooth bending stiffness profile that minimizes abrupt changes in stiffness. A catheter device includes a microfabricated inner shaft having a plurality of gaps, and an outer member comprising a polymer material disposed within the gaps. The catheter device provides non-linear bending stiffness such that bending becomes more difficult as the bend angle increases.

19 Claims, 12 Drawing Sheets

(56) References Cited

U.S. PATENT DOCUMENTS 4,163,406 A 8/1979 Crawford
4,239,069 A 12/1980 Zimmerman
4,416,312 A 11/1983 Oestberg
4,688,540 A 8/1987 Ono
4,719,924 A 1/1988 Crittenden et al.
4,801,297 A 1/1989 Mueller
4,846,186 A 7/1989 Box et al.
4,895,168 A 1/1990 Machek
4,989,608 A 2/1991 Ratner
5,047,045 A 9/1991 Arney et al.
5,069,217 A 12/1991 Fleischhacker, Jr.
5,084,022 A 1/1992 Claude
5,095,915 A 3/1992 Engelson
5,102,390 A 4/1992 Crittenden et al.
5,144,959 A 9/1992 Gambale et al.
5,147,317 A 9/1992 Shank et al.
5,154,725 A 10/1992 Leopold
5,174,302 A 12/1992 Palmer
5,315,996 A 5/1994 Lundquist
5,326,374 A 7/1994 Ilbawi et al.
5,345,945 A 9/1994 Hodgson et al.
5,366,464 A 11/1994 Belknap
5,372,587 A 12/1994 Hammerslag et al.
5,381,782 A 1/1995 Delarama et al.
5,382,259 A 1/1995 Phelps et al.
5,385,152 A 1/1995 Abele et al.
5,437,288 A 8/1995 Schwartz et al.
5,441,483 A 8/1995 Avitall
D363,544 S 10/1995 Rowland et al.
D363,776 S 10/1995 Rowland et al.
5,506,682 A 4/1996 Pryor
5,507,751 A 4/1996 Goode et al.
5,551,444 A 9/1996 Finlayson
5,554,114 A 9/1996 Wallace et al.
5,569,218 A 10/1996 Berg
5,573,520 A 11/1996 Schwartz et al.
5,573,867 A 11/1996 Zafred et al.
5,606,981 A 3/1997 Tartacower et al.
5,659,205 A 8/1997 Weisser
5,673,707 A 10/1997 Chandrasekaran
5,676,659 A 10/1997 Mcgurk
5,685,568 A 11/1997 Pirrello
5,685,868 A 11/1997 Lundquist
5,690,120 A 11/1997 Jacobsen et al.
5,706,826 A 1/1998 Schwager
5,741,429 A 4/1998 Donadio et al.
5,746,701 A 5/1998 Noone
5,772,609 A * 6/1998 Nguyen ................ A61M 25/09 600/585
5,792,154 A 8/1998 Doan et al.
5,797,857 A 8/1998 Obitsu
5,800,454 A 9/1998 Jacobsen et al.
5,833,631 A 11/1998 Nguyen
5,833,632 A 11/1998 Jacobsen et al.
5,842,461 A 12/1998 Azuma
5,860,963 A 1/1999 Azam et al.
5,876,356 A 3/1999 Viera et al.
5,911,715 A 6/1999 Berg et al.
5,911,717 A 6/1999 Jacobsen et al.
5,916,194 A 6/1999 Jacobsen et al.
5,931,830 A 8/1999 Jacobsen et al.
5,954,672 A 9/1999 Schwager
6,004,279 A 12/1999 Crowley et al.
6,014,919 A 1/2000 Jacobsen
6,017,319 A 1/2000 Jacobsen et al.
6,022,343 A 2/2000 Johnson et al.
6,022,369 A 2/2000 Jacobsen et al.
6,027,526 A 2/2000 Limon et al.
6,027,863 A 2/2000 Donadio, III
6,033,288 A 3/2000 Weisshaus et al.
6,033,394 A 3/2000 Vidlund et al.
6,056,702 A 5/2000 Lorenzo
6,063,101 A 5/2000 Jacobsen et al.
6,110,164 A 8/2000 Vidlund
6,132,389 A 10/2000 Cornish et al.
6,139,510 A * 10/2000 Palermo ................ A61M 25/09 600/585
6,139,511 A 10/2000 Huter et al.
D435,909 S 1/2001 Ogino et al.
6,168,570 B1 1/2001 Ferrera
6,179,828 B1 1/2001 Mottola et al.
6,183,410 B1 2/2001 Jacobsen et al.
6,183,420 B1 2/2001 Douk et al.
6,214,042 B1 4/2001 Jacobsen et al.
6,228,073 B1 5/2001 Noone et al.
6,245,030 B1 6/2001 Dubois et al.
6,251,086 B1 6/2001 Cornelius et al.
6,260,458 B1 7/2001 Jacobsen et al.
6,261,246 B1 7/2001 Pantages et al.
6,273,881 B1 8/2001 Kiemeneij
6,302,870 B1 10/2001 Jacobsen et al.
6,306,105 B1 10/2001 Rooney et al.
6,346,091 B1 2/2002 Jacobsen et al.
6,356,791 B1 3/2002 Westlund et al.
6,402,706 B2 6/2002 Richardson et al.
6,428,489 B1 8/2002 Jacobsen et al.
6,431,039 B1 8/2002 Jacobsen et al.
6,436,056 B1 8/2002 Wang et al.
6,440,088 B1 8/2002 Jacobsen et al.
6,458,867 B1 10/2002 Wang et al.
6,464,651 B1 10/2002 Hiejima et al.
6,492,615 B1 12/2002 Flanagan
6,494,894 B2 12/2002 Mirarchi
6,527,732 B1 3/2003 Strauss et al.
6,527,746 B1 3/2003 Oslund et al.
6,553,880 B2 4/2003 Jacobsen et al.
6,554,820 B1 4/2003 Wendlandt et al.
6,558,355 B1 5/2003 Metzger et al.
6,579,246 B2 6/2003 Jacobsen et al.
6,602,207 B1 8/2003 Mam et al.
6,606,985 B2 8/2003 Negishi
6,610,046 B1 8/2003 Usami et al.
6,627,724 B2 9/2003 Meijs et al.
6,648,874 B2 * 11/2003 Parisi ...................... A61L 29/12 604/525
6,652,508 B2 11/2003 Griffin et al.
6,671,560 B2 12/2003 Westlund et al.
6,766,720 B1 7/2004 Jacobsen et al.
6,805,676 B2 10/2004 Klint
6,866,642 B2 3/2005 Kellerman et al.
7,001,369 B2 * 2/2006 Griffin .............. A61M 25/0054 604/524
RE39,018 E 3/2006 Azuma et al.
7,024,885 B2 4/2006 Villalobos
7,097,624 B2 8/2006 Campion et al.
7,110,910 B1 9/2006 Deffenbaugh et al.
7,128,718 B2 10/2006 Hojeibane et al.
7,172,587 B2 2/2007 Poole et al.
7,182,735 B2 2/2007 Shireman et al.
7,276,062 B2 10/2007 Mcdaniel et al.
7,338,345 B2 3/2008 Fujinami
7,421,929 B2 9/2008 French
7,494,474 B2 2/2009 Richardson et al.
7,507,246 B2 3/2009 Mcguckin et al.
D598,094 S 8/2009 Alber
7,621,880 B2 11/2009 Ryan et al.
7,637,875 B2 12/2009 Itou
7,641,622 B2 1/2010 Satou et al.
D611,596 S 3/2010 Kousai et al.
7,670,302 B2 3/2010 Griffin et al.
7,699,792 B2 4/2010 Hofmann et al.
7,722,545 B2 5/2010 Bertsch
7,722,552 B2 5/2010 Aimi et al.
7,744,545 B2 6/2010 Aimi et al.
7,747,314 B2 6/2010 Parins et al.
7,753,859 B2 7/2010 Kinoshita et al.
7,766,896 B2 8/2010 Kornkven et al.
7,769,839 B2 8/2010 Boivie et al.
7,785,273 B2 8/2010 Eskuri
7,789,839 B2 9/2010 Lupton
7,806,837 B2 10/2010 Rasmussen et al.
7,878,984 B2 2/2011 Jacobsen et al.
7,883,474 B1 2/2011 Mirigian et al.
7,914,467 B2 3/2011 Layman et al.

(56) References Cited

U.S. PATENT DOCUMENTS

| | | | |
|---|---|---|---|
| 7,942,832 B2 | 5/2011 | Kanuka et al. | |
| 7,967,762 B2 | 6/2011 | Corl et al. | |
| 7,989,042 B2 * | 8/2011 | Obara | A61M 25/0052 600/300 |
| 8,007,434 B2 | 8/2011 | Olson | |
| 8,043,314 B2 | 10/2011 | Noriega et al. | |
| 8,048,004 B2 | 11/2011 | Davis et al. | |
| 8,092,444 B2 | 1/2012 | Lentz et al. | |
| 8,105,246 B2 | 1/2012 | Voeller et al. | |
| 8,128,579 B2 | 3/2012 | Chen et al. | |
| 8,128,580 B2 | 3/2012 | Fujimagari et al. | |
| 8,137,293 B2 | 3/2012 | Zhou et al. | |
| 8,167,821 B2 | 5/2012 | Sharrow | |
| 8,257,279 B2 | 9/2012 | Jacobsen | |
| 8,292,827 B2 | 10/2012 | Musbach et al. | |
| 8,292,828 B2 | 10/2012 | Uihlein | |
| 8,357,140 B2 | 1/2013 | Majercak et al. | |
| 8,376,865 B2 | 2/2013 | Forster et al. | |
| 8,376,961 B2 | 2/2013 | Layman et al. | |
| 8,377,056 B2 | 2/2013 | Oyola et al. | |
| 8,409,114 B2 | 4/2013 | Parins | |
| 8,409,169 B1 | 4/2013 | Moss | |
| 8,444,577 B2 | 5/2013 | Bunch et al. | |
| 8,454,535 B2 | 6/2013 | Majercak et al. | |
| 8,460,213 B2 | 6/2013 | Northrop | |
| 8,465,469 B2 | 6/2013 | Brightbill | |
| 8,468,919 B2 | 6/2013 | Christian et al. | |
| 8,500,658 B2 | 8/2013 | Boyle et al. | |
| 8,517,959 B2 | 8/2013 | Kurosawa et al. | |
| 8,535,243 B2 | 9/2013 | Shireman | |
| 8,540,648 B2 | 9/2013 | Uihlein | |
| 8,540,668 B2 | 9/2013 | Griffin et al. | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,585,643 B2 | 11/2013 | Vo et al. | |
| 8,622,931 B2 | 1/2014 | Teague et al. | |
| 8,622,933 B2 | 1/2014 | Maki et al. | |
| 8,636,270 B2 | 1/2014 | Ostrovsky | |
| 8,728,075 B2 | 5/2014 | Wu et al. | |
| 8,758,269 B2 | 6/2014 | Miyata et al. | |
| 8,784,337 B2 | 7/2014 | Voeller et al. | |
| 8,795,202 B2 | 8/2014 | Northrop et al. | |
| 8,795,254 B2 | 8/2014 | Layman et al. | |
| 8,821,477 B2 | 9/2014 | Northrop et al. | |
| 8,870,790 B2 | 10/2014 | Davis et al. | |
| 8,900,163 B2 | 12/2014 | Jacobsen et al. | |
| 8,915,865 B2 | 12/2014 | Jacobsen et al. | |
| 8,932,235 B2 | 1/2015 | Jacobsen et al. | |
| 8,936,558 B2 | 1/2015 | Jacobsen et al. | |
| 8,939,916 B2 | 1/2015 | Jacobsen et al. | |
| 8,956,310 B2 | 2/2015 | Miyata et al. | |
| 9,011,511 B2 | 4/2015 | Gregorich et al. | |
| 9,067,332 B2 | 6/2015 | Lippert et al. | |
| 9,067,333 B2 | 6/2015 | Lippert et al. | |
| 9,072,873 B2 | 7/2015 | Lippert et al. | |
| 9,072,874 B2 | 7/2015 | Northrop et al. | |
| D742,000 S | 10/2015 | Kanazawa | |
| 9,162,040 B2 | 10/2015 | Vo et al. | |
| 9,227,037 B2 | 1/2016 | Northrop | |
| 9,254,143 B2 | 2/2016 | Huynh et al. | |
| 9,364,589 B2 | 6/2016 | Cage et al. | |
| 9,375,234 B2 | 6/2016 | Vrba | |
| 9,433,762 B2 | 9/2016 | Griffin et al. | |
| 9,439,557 B2 | 9/2016 | Boulais | |
| 9,550,013 B2 | 1/2017 | Kawasaki | |
| 9,616,195 B2 | 4/2017 | Lippert et al. | |
| 9,623,212 B2 | 4/2017 | Tano et al. | |
| 9,662,798 B2 | 5/2017 | Christian et al. | |
| 9,700,702 B2 | 7/2017 | Tano et al. | |
| 9,808,595 B2 | 11/2017 | Turnlund et al. | |
| 9,839,764 B2 | 12/2017 | Chouinard | |
| 9,848,882 B2 | 12/2017 | Lippert | |
| D809,138 S | 1/2018 | Khan et al. | |
| 9,950,137 B2 | 4/2018 | Lippert et al. | |
| 9,999,748 B2 | 6/2018 | Cajamarca et al. | |
| 10,016,210 B2 | 7/2018 | Lenker et al. | |
| 10,028,666 B2 | 7/2018 | Gregorich | |
| 10,052,013 B2 | 8/2018 | Boulais | |
| 10,149,608 B2 | 12/2018 | Fujitani | |
| D839,426 S | 1/2019 | Bajwa | |
| D847,335 S | 4/2019 | Kuwada | |
| 10,252,024 B2 | 4/2019 | Northrop | |
| D855,180 S | 7/2019 | Haefliger | |
| 10,350,383 B2 | 7/2019 | Shuman | |
| 10,363,389 B2 | 7/2019 | Lippert et al. | |
| D855,800 S | 8/2019 | Gabay et al. | |
| 10,420,537 B2 | 9/2019 | Salahieh et al. | |
| 10,441,746 B2 | 10/2019 | Besselink | |
| 10,456,556 B2 | 10/2019 | Cabiri | |
| 10,639,456 B2 | 5/2020 | Peralta | |
| 10,668,258 B1 | 6/2020 | Calhoun et al. | |
| 10,675,057 B2 | 6/2020 | Krieger et al. | |
| 10,675,444 B2 | 6/2020 | Kauphusman et al. | |
| 10,758,710 B2 | 9/2020 | Romano | |
| 10,806,893 B2 | 10/2020 | Jaroch | |
| 10,821,268 B2 | 11/2020 | Snyder et al. | |
| 10,835,183 B2 | 11/2020 | Sham et al. | |
| 11,007,345 B2 | 5/2021 | Cottone | |
| 11,052,226 B2 | 7/2021 | Salahieh et al. | |
| 11,052,228 B2 | 7/2021 | Lippert et al. | |
| 11,141,566 B2 | 10/2021 | Cabiri | |
| D946,148 S | 3/2022 | Takemoto | |
| 11,278,704 B2 | 3/2022 | Pleijers | |
| 11,305,095 B2 * | 4/2022 | Snyder | A61M 25/0138 |
| 11,317,938 B2 | 5/2022 | Lenker et al. | |
| 11,369,351 B2 | 6/2022 | Davis et al. | |
| 11,471,645 B2 | 10/2022 | Mcniven et al. | |
| 11,497,512 B2 | 11/2022 | Wallace et al. | |
| 11,565,093 B2 | 1/2023 | Kirt et al. | |
| D980,427 S | 3/2023 | Method et al. | |
| 11,679,236 B2 | 6/2023 | Von et al. | |
| 11,724,065 B2 | 8/2023 | Tilson et al. | |
| 11,724,068 B2 | 8/2023 | Von et al. | |
| 11,759,217 B2 | 9/2023 | Keating et al. | |
| 11,766,539 B2 | 9/2023 | Yee et al. | |
| D1,014,751 S | 2/2024 | Shih | |
| 11,918,753 B2 | 3/2024 | Moquin et al. | |
| 11,957,312 B2 | 4/2024 | Boulais | |
| 12,178,975 B2 * | 12/2024 | Lippert | A61M 25/09 |
| 2001/0009980 A1 | 7/2001 | Richardson et al. | |
| 2001/0044624 A1 | 11/2001 | Seraj et al. | |
| 2002/0013540 A1 | 1/2002 | Jacobsen et al. | |
| 2002/0019599 A1 | 2/2002 | Rooney et al. | |
| 2002/0049392 A1 | 4/2002 | Demello | |
| 2002/0062524 A1 | 5/2002 | Vogland et al. | |
| 2002/0078808 A1 | 6/2002 | Jacobsen et al. | |
| 2002/0082524 A1 | 6/2002 | Anderson et al. | |
| 2003/0009208 A1 | 1/2003 | Snyder et al. | |
| 2003/0023190 A1 | 1/2003 | Cox | |
| 2003/0060732 A1 | 3/2003 | Jacobsen et al. | |
| 2003/0069521 A1 | 4/2003 | Reynolds et al. | |
| 2003/0069522 A1 | 4/2003 | Jacobsen et al. | |
| 2003/0093059 A1 | 5/2003 | Griffin et al. | |
| 2003/0125641 A1 | 7/2003 | Jafari et al. | |
| 2004/0039371 A1 | 2/2004 | Tockman et al. | |
| 2004/0054349 A1 | 3/2004 | Brightbill | |
| 2004/0087933 A1 | 5/2004 | Lee et al. | |
| 2004/0093060 A1 | 5/2004 | Seguin et al. | |
| 2004/0102719 A1 | 5/2004 | Keith et al. | |
| 2004/0102720 A1 | 5/2004 | Kellerman et al. | |
| 2004/0111044 A1 | 6/2004 | Davis et al. | |
| 2004/0122340 A1 | 6/2004 | Vrba et al. | |
| 2004/0167437 A1 | 8/2004 | Sharrow et al. | |
| 2004/0167440 A1 | 8/2004 | Sharrow | |
| 2004/0167443 A1 | 8/2004 | Shireman et al. | |
| 2004/0171996 A1 | 9/2004 | Kiemeneij | |
| 2004/0181174 A2 | 9/2004 | Davis et al. | |
| 2004/0186485 A1 | 9/2004 | Kear | |
| 2004/0193140 A1 | 9/2004 | Griffin et al. | |
| 2004/0225292 A1 | 11/2004 | Sasso et al. | |
| 2004/0254450 A1 | 12/2004 | Griffin et al. | |
| 2005/0054953 A1 | 3/2005 | Ryan et al. | |
| 2005/0065456 A1 | 3/2005 | Eskuri | |

(56) References Cited

U.S. PATENT DOCUMENTS

2005/0124976 A1 6/2005 Devens et al.
2005/0216049 A1 9/2005 Jones et al.
2005/0274384 A1 12/2005 Tran et al.
2006/0041186 A1 2/2006 Vancaillie
2006/0074442 A1 4/2006 Noriega et al.
2006/0089618 A1 4/2006 Mcferran et al.
2006/0112802 A1 6/2006 Fujinami
2006/0121218 A1 6/2006 Obara et al.
2006/0189896 A1 8/2006 Davis et al.
2006/0241519 A1 10/2006 Hojeibane et al.
2006/0247661 A1 11/2006 Richards et al.
2006/0262474 A1 11/2006 Chen et al.
2006/0264904 A1* 11/2006 Kerby ............... A61M 25/0043 604/523
2007/0010786 A1 1/2007 Casey et al.
2007/0055302 A1 3/2007 Henry et al.
2007/0100285 A1 5/2007 Griffin et al.
2007/0112331 A1* 5/2007 Weber ............... A61M 25/0054 604/530
2007/0135763 A1 6/2007 Musbach et al.
2007/0142893 A1 6/2007 Buiser et al.
2007/0167876 A1 7/2007 Euteneuer et al.
2007/0185415 A1 8/2007 Ressemann et al.
2007/0208405 A1 9/2007 Goodin et al.
2007/0213689 A1 9/2007 Grewe et al.
2007/0221230 A1 9/2007 Thompson et al.
2007/0233039 A1 10/2007 Mitelberg
2007/0250036 A1 10/2007 Volk et al.
2007/0287955 A1 12/2007 Layman et al.
2008/0021347 A1 1/2008 Jacobsen et al.
2008/0021401 A1 1/2008 Jacobsen et al.
2008/0021404 A1 1/2008 Jacobsen et al.
2008/0021406 A1 1/2008 Jacobsen et al.
2008/0033421 A1 2/2008 Davis et al.
2008/0064989 A1 3/2008 Chen et al.
2008/0077049 A1 3/2008 Hirshman
2008/0086854 A1 4/2008 Boyd et al.
2008/0097246 A1 4/2008 Stafford
2008/0097247 A1 4/2008 Eskuri
2008/0097248 A1 4/2008 Munoz et al.
2008/0119869 A1 5/2008 Teague et al.
2008/0122226 A1 5/2008 Madison
2008/0125674 A1 5/2008 Bilecen et al.
2008/0140101 A1 6/2008 Carley et al.
2008/0147170 A1 6/2008 Vrba
2008/0188298 A1 8/2008 Seelig et al.
2008/0188928 A1 8/2008 Salahieh et al.
2008/0200839 A1 8/2008 Bunch et al.
2008/0262474 A1 10/2008 Northrop
2008/0269641 A1 10/2008 O'Shaughnessy et al.
2008/0319525 A1 12/2008 Tieu et al.
2009/0036832 A1 2/2009 Skujins et al.
2009/0036833 A1 2/2009 Parins
2009/0043283 A1 2/2009 Turnlund et al.
2009/0043372 A1 2/2009 Northrop et al.
2009/0043483 A1 2/2009 Abe et al.
2009/0118675 A1 5/2009 Czyscon et al.
2009/0118704 A1 5/2009 Sharrow et al.
2009/0163945 A1 6/2009 Richard et al.
2009/0177119 A1 7/2009 Heidner et al.
2009/0177185 A1 7/2009 Northrop
2009/0254000 A1 10/2009 Layman et al.
2009/0292225 A1 11/2009 Chen et al.
2009/0318892 A1 12/2009 Aboytes et al.
2010/0063479 A1* 3/2010 Merdan ................. A61M 25/09 604/528
2010/0069882 A1 3/2010 Jennings et al.
2010/0114017 A1 5/2010 Lenker et al.
2010/0114302 A1 5/2010 Tzafriri et al.
2010/0139465 A1 6/2010 Christian et al.
2010/0145308 A1 6/2010 Layman et al.
2010/0228150 A1 9/2010 Zimmerman et al.
2010/0256527 A1 10/2010 Lippert et al.
2010/0256528 A1 10/2010 Lippert et al.
2010/0256601 A1 10/2010 Lippert et al.
2010/0256602 A1 10/2010 Lippert et al.
2010/0256603 A1* 10/2010 Lippert ............. A61M 25/0051 604/524
2010/0256604 A1 10/2010 Lippert et al.
2010/0256605 A1 10/2010 Lippert et al.
2010/0256606 A1 10/2010 Lippert et al.
2010/0318066 A1 12/2010 Miyata et al.
2011/0011226 A1 1/2011 Tsurusawa et al.
2011/0022003 A1 1/2011 Tekulve
2011/0160680 A1 6/2011 Cage et al.
2011/0245807 A1 10/2011 Sakata et al.
2011/0245808 A1* 10/2011 Voeller .............. A61M 25/0054 604/528
2011/0251519 A1 10/2011 Romoscanu
2011/0313417 A1 12/2011 De et al.
2012/0046575 A1 2/2012 Brown
2012/0065623 A1 3/2012 Nelson et al.
2012/0158034 A1 6/2012 Wilson et al.
2012/0209073 A1 8/2012 Mcweeney et al.
2012/0239074 A1 9/2012 Aboytes et al.
2012/0271397 A1 10/2012 Muzslay et al.
2012/0289938 A1 11/2012 Northrop et al.
2013/0018359 A1 1/2013 Coyle
2013/0096553 A1 4/2013 Hill et al.
2013/0110000 A1 5/2013 Tully et al.
2013/0131642 A1 5/2013 Miyata et al.
2013/0144267 A1 6/2013 Chan et al.
2013/0184703 A1 7/2013 Shireman et al.
2013/0226033 A1 8/2013 Eskuri
2013/0255456 A1 10/2013 Christian et al.
2013/0274784 A1 10/2013 Lenker et al.
2014/0012281 A1 1/2014 Wang et al.
2014/0031719 A1 1/2014 Kanazawa
2014/0058324 A1 2/2014 Salahieh et al.
2014/0094787 A1 4/2014 Reynolds
2014/0187983 A1 7/2014 Anderson
2014/0257363 A1 9/2014 Lippert
2014/0276109 A1 9/2014 Gregorich
2014/0276117 A1 9/2014 Burkett
2014/0276787 A1 9/2014 Wang et al.
2014/0279109 A1 9/2014 Vasquez et al.
2014/0309657 A1 10/2014 Ben-Ami
2014/0336620 A1 11/2014 Layman et al.
2014/0343538 A1 11/2014 Lenker et al.
2015/0011834 A1 1/2015 Ayala et al.
2015/0011964 A1 1/2015 Abner et al.
2015/0057639 A1 2/2015 Storbeck et al.
2015/0190614 A1 7/2015 Uihlein
2015/0190615 A1 7/2015 Shaltis
2015/0216533 A1 8/2015 Gray et al.
2015/0238734 A1 8/2015 Kanazawa
2015/0290432 A1 10/2015 Mathews et al.
2015/0297863 A1 10/2015 Hannon et al.
2015/0305710 A1 10/2015 Stigall et al.
2015/0306355 A1 10/2015 Idstrom
2016/0001048 A1 1/2016 Koike
2016/0008585 A1 1/2016 Tano
2016/0045101 A1 2/2016 Nakatate et al.
2016/0058382 A1 3/2016 Burkett et al.
2016/0089128 A1 3/2016 Weber et al.
2016/0113793 A1 4/2016 Nishigishi
2016/0135827 A1 5/2016 Elsesser et al.
2016/0199620 A1 7/2016 Pokorney et al.
2016/0235337 A1 8/2016 Govari et al.
2016/0287054 A1 10/2016 Fujitani
2016/0310702 A1 10/2016 Cabiri
2016/0361520 A1 12/2016 Braun
2016/0367788 A1 12/2016 Jimenez et al.
2016/0375226 A1 12/2016 Nabeshima et al.
2017/0047740 A1 2/2017 Narla
2017/0049594 A1 2/2017 Banas et al.
2017/0095138 A1 4/2017 Nakade et al.
2017/0136213 A1 5/2017 Kauphusman et al.
2017/0189643 A1 7/2017 Christian et al.
2017/0203076 A1 7/2017 Groneberg et al.
2017/0215954 A1 8/2017 Datta et al.
2017/0234411 A1 8/2017 Dewaele et al.
2017/0281909 A1* 10/2017 Northrop .......... A61M 25/0013
2018/0015260 A1 1/2018 Sano et al.

(56) References Cited

U.S. PATENT DOCUMENTS

| | | | | |
|---|---|---|---|---|
| 2018/0015261 | A1 | 1/2018 | Lippert et al. | |
| 2018/0015262 | A1 | 1/2018 | Lippert et al. | |
| 2018/0015263 | A1 | 1/2018 | Lippert et al. | |
| 2018/0028177 | A1 | 2/2018 | Van et al. | |
| 2018/0071496 | A1* | 3/2018 | Snyder | A61M 25/0052 |
| 2018/0177517 | A1 | 6/2018 | Lippert et al. | |
| 2018/0185619 | A1 | 7/2018 | Batman et al. | |
| 2018/0193603 | A1 | 7/2018 | Falb et al. | |
| 2018/0193607 | A1 | 7/2018 | Lippert et al. | |
| 2018/0207407 | A1 | 7/2018 | Tanigaki | |
| 2019/0008639 | A1 | 1/2019 | Landon et al. | |
| 2019/0060612 | A1 | 2/2019 | Besselink | |
| 2019/0105463 | A1 | 4/2019 | Christian et al. | |
| 2019/0175869 | A1 | 6/2019 | Kirt et al. | |
| 2019/0247621 | A1* | 8/2019 | Romano | A61M 25/0051 |
| 2019/0255290 | A1* | 8/2019 | Snyder | A61M 25/0054 |
| 2019/0290883 | A1* | 9/2019 | Lippert | A61M 25/0051 |
| 2019/0358434 | A1 | 11/2019 | Fuller et al. | |
| 2020/0016378 | A1 | 1/2020 | Williams et al. | |
| 2020/0054860 | A1 | 2/2020 | Mcelhaney et al. | |
| 2020/0094027 | A1 | 3/2020 | Davis | |
| 2020/0121308 | A1* | 4/2020 | Davis | A61M 25/0051 |
| 2020/0222666 | A1 | 7/2020 | Chan et al. | |
| 2020/0222672 | A1 | 7/2020 | Davis et al. | |
| 2020/0330734 | A1 | 10/2020 | Sugita et al. | |
| 2020/0345975 | A1 | 11/2020 | Snyder | |
| 2021/0008351 | A1* | 1/2021 | Snyder | A61M 25/09 |
| 2021/0022748 | A1 | 1/2021 | Lorenzo | |
| 2021/0162184 | A1 | 6/2021 | Lippert et al. | |
| 2021/0178128 | A1 | 6/2021 | Lippert et al. | |
| 2021/0213241 | A1 | 7/2021 | Christian et al. | |
| 2021/0228845 | A1 | 7/2021 | Lippert et al. | |
| 2021/0283372 | A1 | 9/2021 | Murphy | |
| 2021/0283380 | A1 | 9/2021 | Lippert et al. | |
| 2021/0307766 | A1 | 10/2021 | Keating et al. | |
| 2021/0346656 | A1 | 11/2021 | Lippert et al. | |
| 2022/0039644 | A1 | 2/2022 | Dayton et al. | |
| 2022/0047845 | A1 | 2/2022 | Niederhauser et al. | |
| 2022/0105312 | A1 | 4/2022 | Davis | |
| 2022/0105318 | A1 | 4/2022 | Davis et al. | |
| 2022/0118225 | A1 | 4/2022 | Snyder et al. | |
| 2022/0176075 | A1 | 6/2022 | Mcdermott et al. | |
| 2022/0211981 | A1 | 7/2022 | Darbellay et al. | |
| 2022/0218358 | A1 | 7/2022 | Dagan et al. | |
| 2022/0273474 | A1 | 9/2022 | Koop et al. | |
| 2022/0280147 | A1 | 9/2022 | Davis | |
| 2022/0296850 | A1 | 9/2022 | Lippert | |
| 2022/0323166 | A1 | 10/2022 | Tilson et al. | |
| 2022/0378459 | A1 | 12/2022 | Lippert | |
| 2023/0010697 | A1 | 1/2023 | Sharma et al. | |
| 2023/0069698 | A1 | 3/2023 | Hallauer et al. | |
| 2023/0082226 | A1 | 3/2023 | Lippert et al. | |
| 2023/0285720 | A1 | 9/2023 | Isogai | |
| 2023/0405276 | A1 | 12/2023 | Cabiri | |
| 2024/0123196 | A1 | 4/2024 | Lippert et al. | |
| 2024/0198059 | A1 | 6/2024 | Lippert et al. | |
| 2024/0299710 | A1 | 9/2024 | Davis et al. | |

FOREIGN PATENT DOCUMENTS

| | | | |
|---|---|---|---|
| AU | 07745/59 | B2 | 7/2004 |
| AU | 2008229892 | A1 | 10/2008 |
| BR | 9709363 | A | 1/2000 |
| BR | 9712829 | A | 1/2000 |
| CA | 2255781 | A1 | 11/1997 |
| CA | 2266685 | A1 | 3/1998 |
| CA | 2395149 | A1 | 6/2001 |
| CN | 1230914 | A | 10/1999 |
| CN | 1324285 | A | 11/2001 |
| CN | 1422673 | A | 6/2003 |
| CN | 1518428 | A | 8/2004 |
| CN | 1781684 | A | 6/2006 |
| CN | 1897892 | A | 1/2007 |
| CN | 101001660 | A | 7/2007 |
| CN | 101209365 | A | 7/2008 |
| CN | 101304778 | A | 11/2008 |
| CN | 201239164 | Y | 5/2009 |
| CN | 101815553 | A | 8/2010 |
| CN | 102049085 | A | 5/2011 |
| CN | 102107041 | A | 6/2011 |
| CN | 102438691 | A | 5/2012 |
| CN | 102548603 | A | 7/2012 |
| CN | 102824681 | A | 12/2012 |
| CN | 102847225 | A | 1/2013 |
| CN | 103301553 | A | 9/2013 |
| CN | 103566457 | A | 2/2014 |
| CN | 103764012 | A | 4/2014 |
| CN | 103799980 | A | 5/2014 |
| CN | 103860265 | A | 6/2014 |
| CN | 104271035 | A | 1/2015 |
| CN | 104302345 | A | 1/2015 |
| CN | 104427950 | A | 3/2015 |
| CN | 104602616 | A | 5/2015 |
| CN | 104602718 | A | 5/2015 |
| CN | 104619247 | A | 5/2015 |
| CN | 104759022 | A | 7/2015 |
| CN | 104812420 | A | 7/2015 |
| CN | 105209102 | A | 12/2015 |
| CN | 105228536 | A | 1/2016 |
| CN | 105361918 | A | 3/2016 |
| CN | 105545375 | A | 5/2016 |
| CN | 105582611 | A | 5/2016 |
| CN | 105682725 | A | 6/2016 |
| CN | 105682729 | A | 6/2016 |
| CN | 105828690 | A | 8/2016 |
| CN | 105979880 | A | 9/2016 |
| CN | 106455910 | A | 2/2017 |
| CN | 107206216 | A | 9/2017 |
| CN | 109715245 | A | 5/2019 |
| CN | 109789296 | A | 5/2019 |
| CN | 110691626 | A | 1/2020 |
| DE | 60036882 | T2 | 7/2008 |
| DE | 69738235 | T2 | 7/2008 |
| EP | 0521595 | A2 | 1/1993 |
| EP | 0921754 | A1 | 6/1999 |
| EP | 0998323 | A1 | 5/2000 |
| EP | 0934141 | B1 | 11/2005 |
| EP | 1239901 | B1 | 10/2007 |
| EP | 1940498 | A1 | 7/2008 |
| EP | 2964305 | A2 | 1/2016 |
| EP | 2414022 | B1 | 8/2017 |
| EP | 3866902 | A1 | 8/2021 |
| ES | 2293660 | T3 | 3/2008 |
| GB | 2478988 | A | 9/2011 |
| JP | 59-102509 | A | 6/1984 |
| JP | 06-154335 | A | 6/1994 |
| JP | 07-008560 | A | 1/1995 |
| JP | 08-215313 | A | 8/1996 |
| JP | 08-243168 | A | 9/1996 |
| JP | 08-243169 | A | 9/1996 |
| JP | 08-308934 | A | 11/1996 |
| JP | 11-294497 | A | 10/1999 |
| JP | 2000-503225 | A | 3/2000 |
| JP | 2000-116787 | A | 4/2000 |
| JP | 2000-126301 | A | 5/2000 |
| JP | 2000-511094 | A | 8/2000 |
| JP | 2000-343313 | A | 12/2000 |
| JP | 2001-500808 | A | 1/2001 |
| JP | 2002-543896 | A | 12/2002 |
| JP | 2003-011117 | A | 1/2003 |
| JP | 2004-025340 | A | 1/2004 |
| JP | 2004-136121 | A | 5/2004 |
| JP | 2004-329552 | A | 11/2004 |
| JP | 2004-535233 | A | 11/2004 |
| JP | 2005-514115 | A | 5/2005 |
| JP | 2005-533594 | A | 11/2005 |
| JP | 2005-534407 | A | 11/2005 |
| JP | 2007-514458 | A | 6/2007 |
| JP | 2007-313638 | A | 12/2007 |
| JP | 2008-178656 | A | 8/2008 |
| JP | 2008-536639 | A | 9/2008 |
| JP | 2010-029736 | A | 2/2010 |
| JP | 2010-503484 | A | 2/2010 |
| JP | 2010-535583 | A | 11/2010 |

(56) References Cited

FOREIGN PATENT DOCUMENTS

| | | | |
|---|---|---|---|
| JP | 2010-535588 | A | 11/2010 |
| JP | 2011-206175 | A | 10/2011 |
| JP | 4805208 | B2 | 11/2011 |
| JP | 4845313 | B2 | 12/2011 |
| JP | 2012-502743 | A | 2/2012 |
| JP | 2013-106854 | A | 6/2013 |
| JP | 2013-523282 | A | 6/2013 |
| JP | 2013-176560 | A | 9/2013 |
| JP | 2014-023727 | A | 2/2014 |
| JP | 2015-073861 | A | 4/2015 |
| JP | 2015-181723 | A | 10/2015 |
| JP | 2015-186427 | A | 10/2015 |
| JP | 2016-013269 | A | 1/2016 |
| JP | 2017-169253 | A | 9/2017 |
| JP | 2021-514700 | A | 6/2021 |
| KR | 2000-0015896 | A | 3/2000 |
| KR | 10-2000-0036139 | A | 6/2000 |
| NL | 2017570 | B1 | 4/2018 |
| RU | 91674 | U1 | 2/2010 |
| TW | 412468 | B | 11/2000 |
| WO | 94/06503 | A1 | 3/1994 |
| WO | 94/19039 | A1 | 9/1994 |
| WO | 95/24237 | A2 | 9/1995 |
| WO | 97/25914 | A1 | 7/1997 |
| WO | 97/43949 | A1 | 11/1997 |
| WO | 98/55173 | A1 | 12/1998 |
| WO | 98/58697 | A1 | 12/1998 |
| WO | 99/04847 | A1 | 2/1999 |
| WO | 99/53824 | A2 | 10/1999 |
| WO | 2004/011076 | A2 | 2/2004 |
| WO | 2006/025931 | A1 | 3/2006 |
| WO | 2006/058234 | A2 | 6/2006 |
| WO | 2006/113863 | A2 | 10/2006 |
| WO | 2007/050718 | A1 | 5/2007 |
| WO | 2008/034010 | A2 | 3/2008 |
| WO | 2009/020691 | A2 | 2/2009 |
| WO | 2009/020836 | A1 | 2/2009 |
| WO | 2009/020961 | A1 | 2/2009 |
| WO | 2009/020962 | A1 | 2/2009 |
| WO | 2009/143160 | A1 | 11/2009 |
| WO | 2010/077692 | A2 | 7/2010 |
| WO | 2010/115163 | A1 | 10/2010 |
| WO | 2011/123689 | A1 | 10/2011 |
| WO | 2014/005095 | A1 | 1/2014 |
| WO | 2014/066104 | A1 | 5/2014 |
| WO | 2014/077881 | A1 | 5/2014 |
| WO | 2014/138580 | A2 | 9/2014 |
| WO | 2016/047499 | A1 | 3/2016 |
| WO | 2016/117238 | A1 | 7/2016 |
| WO | 2016/136609 | A1 | 9/2016 |
| WO | 2016/152194 | A1 | 9/2016 |
| WO | 2016/158671 | A1 | 10/2016 |
| WO | 2017/151292 | A1 | 9/2017 |
| WO | 2018/017349 | A1 | 1/2018 |
| WO | 2018/017351 | A1 | 1/2018 |
| WO | 2018/218216 | A1 | 11/2018 |
| WO | 2019/039589 | A1 | 2/2019 |
| WO | 2020/217171 | A1 | 10/2020 |
| WO | 2022/159139 | A1 | 7/2022 |

OTHER PUBLICATIONS

Final Office Action received for U.S. Appl. No. 12/753,836 mailed on Feb. 17, 2016.
Final Office Action received for U.S. Appl. No. 16/855,366, mailed on Dec. 8, 2022, 18 pages.
Final Office Action received for U.S. Appl. No. 16/212,425, mailed on Aug. 3, 2020, 14 pages.
Final Office Action received for U.S. Appl. No. 12/753,831, mailed on Aug. 29, 2014.
Final Office Action received for U.S. Appl. No. 12/753,836, mailed on Jan. 9, 2015.
Final Office Action received for U.S. Appl. No. 12/753,836, mailed on Jul. 14, 2017.
Final Office Action received for U.S. Appl. No. 12/753,836, mailed on May 1, 2012.
Final Office Action received for U.S. Appl. No. 12/753,839, mailed on May 31, 2012.
Final Office Action received for U.S. Appl. No. 12/753,842, mailed on Jan. 9, 2013.
Final Office Action received for U.S. Appl. No. 12/753,842, mailed on Sep. 4, 2014.
Final Office Action received for U.S. Appl. No. 12/753,849, mailed on Jun. 6, 2012.
Final Office Action received for U.S. Appl. No. 12/753,849, mailed on Oct. 9, 2013.
Final Office Action received for U.S. Appl. No. 12/753,855, mailed on Apr. 18, 2012.
Final Office Action received for U.S. Appl. No. 12/753,855, mailed on Jan. 13, 2015.
Final Office Action received for U.S. Appl. No. 12/753,858, mailed on Jan. 17, 2014.
Final Office Action received for U.S. Appl. No. 12/753,858, mailed on Jul. 18, 2012.
Final Office Action received for U.S. Appl. No. 12/753,858, mailed on May 28, 2015.
Final Office Action received for U.S. Appl. No. 12/753,858, mailed on Nov. 14, 2018.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 15/606,607, mailed on Nov. 19, 2019.
Final Office Action received for U.S. Appl. No. 15/611,344, mailed on Nov. 12, 2019.
Final Office Action received for U.S. Appl. No. 15/848,878, mailed on Aug. 27, 2020, 13 pages.
Final Office Action received for U.S. Appl. No. 15/848,878, mailed on Sep. 22, 2021, 12 pages.
Final Office Action received for U.S. Appl. No. 16/281,046, mailed on May 11, 2021, 18 pages.
Final Office Action received for U.S. Appl. No. 16/616,220, mailed on Oct. 12, 2022, 17 pages.
Final Office Action received for U.S. Appl. No. 16/742,211, mailed on Mar. 14, 2023, 22 pages.
Final Office Action received for U.S. Appl. No. 17/216,127, mailed on Jun. 13, 2022, 8 pages.
Final Office Action received for U.S. Appl. No. 14/199,675, mailed on May 18, 2017.
Final Office Action received for U.S. Appl. No. 15/611,328, mailed on Sep. 24, 2019.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for application No. PCT/US17/41305 dated Oct. 2, 2017.
International Search Report and Written Opinion for Application PCT/US2017/050602 mailed on Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 mailed on Oct. 2, 2017.
International Search Report and Written Opinion for PCT/US2017/041301 mailed on Oct. 2, 2017.
International Search Report and Written Opinion for PCT/US2017/068056 mailed on Feb. 26, 2018.
International Search Report and Written Opinion for PCT/US2018/034756 mailed on Aug. 14, 2018.
International Search Report and Written Opinion for PCT/US2019/019046, mailed on May 17, 2019.

(56) References Cited

OTHER PUBLICATIONS

International Search Report and Written Opinion for PCT/US2019/021031 mailed on Jun. 18, 2019.
International Search Report and Written Opinion received for PCT Patent Application No. PCT/US2018/034723, mailed on Sep. 5, 2018, 10 pages.
International Search Report and Written Opinion received for PCT Patent Application No. PCT/US2020/030589, mailed on Jul. 17, 2020, 7 pages.
International Search Report and Written Opinion received for PCT Patent Application No. PCT/US2021/053652, mailed on Dec. 28, 2021, 9 pages.
InternationalSearch Report and Written Opinion for application PCT/US2017/050802 mailed on Nov. 7, 2017.
Non-Final Office Action received for U.S. Appl. No. 15/606,607, mailed on Jun. 10, 2020, 26 pages.
Non-Final Office Action received for U.S. Appl. No. 15/611,328, mailed on Jun. 29, 2020, 13 pages.
Supplementary European Search Report received for EP Patent Application No. 21744674.9, mailed on Feb. 7, 2024, 9 pages.
European Search Report received for EP Patent Application No. 21878402, mailed on Aug. 14, 2024, 13 pages.
Intention to grant received for European Patent Application No. 23188821.5, mailed on Aug. 14, 2024, 6 pages.
Final Office Action received for U.S. Appl. No. 17/154,777, mailed on Apr. 17, 2024, 17 pages.
Requirement for Restriction/Election received for U.S. Appl. No. 17/752,600, mailed on Apr. 25, 2024, 5 pages.
Chinese Search Report for Chinese Application No. 201780070242.X, dated Sep. 14, 2016, 4 pages.
International Search Report and Written Opinion received for PCT Patent Application No. PCT/US22/42514, mailed on Dec. 28, 2022, 11 pages.
International Search Report and Written Opinion received for PCT Patent Application No. PCT/US22/42517, mailed on Feb. 7, 2023, 11 pages.
International Search Report and Written Opinion received for PCT Patent Application No. PCT/US2021/053647, mailed on Dec. 28, 2021, 9 pages.
International Search Report and Written Opinion received for PCT Patent Application No. PCT/US21/042753, mailed on Nov. 5, 2021, 14 pages.
International Search Report and Written Opinion received for PCT Patent Application No. PCT/US21/14656, mailed on Apr. 28, 2021, 8 pages.
International Search Report and Written Opinion, PCT App. No. PCT/US2020/013754, mailed on Jun. 9, 2020, 11 pages.
Final Office Action received for U.S. Appl. No. 17/036,302, mailed on Jul. 30, 2024, 17 pages.
Final Office Action received for U.S. Appl. No. 17/382,271, mailed on Sep. 16, 2024, 9 pages.
Final Office Action received for U.S. Appl. No. 17/836,863, mailed on Jun. 25, 2024, 6 pages.
Non-Final Office Action received for U.S. Appl. No. 17/382,271, mailed on May 14, 2024, 22 pages.
Non-Final Office Action received for U.S. Appl. No. 17/493,265, mailed on Jun. 11, 2024, 19 pages.
Non-Final Office Action received for U.S. Appl. No. 17/752,600, mailed on Sep. 10, 2024, 11 pages.
Non-Final Office Action received for U.S. Appl. No. 15/848,878, mailed on Jun. 3, 2021, 13 pages.
Non-Final Office Action received for U.S. Appl. No. 15/917,255, mailed on Aug. 17, 2020, 12 pages.
Non-Final Office Action received for U.S. Appl. No. 16/281,046, mailed on Oct. 29, 2020, 18 pages.
Non-Final Office Action received for U.S. Appl. No. 16/616,139, mailed on Oct. 26, 2021, 11 pages.
Non-Final Office Action received for U.S. Appl. No. 16/616,220, mailed on Jun. 3, 2022, 20 pages.
Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 16/855,366, mailed on Jun. 23, 2021, 15 pages.
Non-Final Office Action received for U.S. Appl. No. 17/036,302, mailed on Mar. 1, 2023, 29 pages.
Non-Final Office Action received for U.S. Appl. No. 17/177,782, mailed on Jan. 23, 2023, 14 pages.
Non-Final Office Action received for U.S. Appl. No. 17/177,782, mailed on Nov. 4, 2022, 7 pages.
Notice of Allowance received for U.S. Appl. No. 16/212,425, mailed on Dec. 23, 2020, 12 pages.
Notice of Allowance received for U.S. Appl. No. 16/212,425, mailed on Jan. 25, 2021, 2 pages.
Office Action received for U.S. Appl. No. 12/633,727, mailed on Oct. 16, 2012.
Office Action received for U.S. Appl. No. 12/753,831, mailed on Feb. 1, 2012.
Office Action received for U.S. Appl. No. 12/753,831, mailed on Mar. 21, 2014.
Office Action received for U.S. Appl. No. 12/753,836, mailed on Dec. 9, 2011.
Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on Feb. 7, 2012.
Office Action received for U.S. Appl. No. 12/753,839, mailed on May 5, 2014.
Office Action received for U.S. Appl. No. 12/753,842, mailed on Aug. 1, 2012.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.
Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.
Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 13/901,375, mailed on Dec. 10, 2015.
Office Action received for U.S. Appl. No. 15/465,399, mailed on Apr. 23, 2018.

(56) References Cited

OTHER PUBLICATIONS

Office Action received for U.S. Appl. No. 15/606,607, mailed on May 14, 2019.
Office Action received for U.S. Appl. No. 15/611,344, mailed on Mar. 26, 2019.
Office Action received for U.S. Appl. No. 15/611,344, mailed on May 21, 2020.
Office Action received for U.S. Appl. No. 15/848,878, mailed on Feb. 5, 2020.
Office Action received for U.S. Appl. No. 15/848,878, mailed on Oct. 29, 2019.
Office Action received for U.S. Appl. No. 16/212,425, mailed on Mar. 16, 2020.
Office Action received for U.S. Appl. No. 12/753,855 mailed on May 5, 2016.
Office Action received for U.S. Appl. No. 13/901,375, mailed on Aug. 1, 2016.
Office Action received for U.S. Appl. No. 14/199,675, mailed on Nov. 3, 2016.
Baz, R.A.; Scheau, C.; Niscoveanu, C.; Bordei, P. Morphometry of the Entire Internal Carotid Artery on CT Angiography. Medicina 2021, 57, 832. https://doi.org/10.3390/medicina57080832 (Year: 2021).
Lauric A, et al. J NeuroIntervent Surg 2014; 6:733-739. doi:10.1136/neurintsurg-2013-010987 (Year: 2013).
Non-Final Office Action received for U.S. Appl. No. 17/036,302, mailed on Nov. 6, 2025, 23 pages.
Non-Final Office Action received for U.S. Appl. No. 17/901,819, mailed on Jun. 30, 2025, 21 pages.
Office Action received for U.S. Appl. No. 15/611,328, mailed on Mar. 27, 2019.
Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).
U.S. Appl. No. 12/753,836, filed Feb. 1, 2012, Office Action.
Penumbra, Inc., Penumbra Augments Vascular Franchise with Latest Indigo System Launch and Expands Medical/Scientific Leadership, Jul. 14, 2020, https://www.penumbrainc.com/penumbra-augments-vascular-franchise-with-latest-indigo-system-launch-and-expands-medical-scientific-leadership/, May 14, 2026.

* cited by examiner

MICROCATHETER DEVICE WITH NON-LINEAR BENDING STIFFNESS

CROSS-REFERENCE TO RELATED APPLICATIONS

This application claims priority to and the benefit of U.S. Provisional Application No. 63/271,114, filed Oct. 22, 2021 and titled "Intravascular Guidewire and Microcatheter System," and to U.S. Provisional Application No. 63/240,845, filed on Sep. 3, 2021 and titled "Microcatheter Device with Non-Linear Bending Stiffness," each of which is incorporated herein by this reference in its entirety.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy over a guidewire. Once in place, the catheter can be used to deliver drugs, stents, embolic devices, radiopaque dyes, or other devices or substances for treating the patient in a desired manner.

In many applications, such an interventional device must be navigated through the tortuous bends and curves of a vasculature passageway to arrive at the targeted anatomy. Such an interventional device requires sufficient flexibility, particularly closer to its distal end, to navigate such tortuous pathways. However, other design aspects must also be considered. For example, the interventional device must also be able to provide sufficient torquability (i.e., the ability to transmit torque applied at the proximal end all the way to the distal end), pushability (i.e., the ability to transmit axial push to the distal end rather than bending and binding intermediate portions), and structural integrity for performing intended medical functions.

It is desirable for catheter devices to have good axial response. In other words, when the user moves the proximal end of the device, he/she expects the distal end to move the same distance. Often, however, as the device is positioned within the bends and curves of the vasculature, much of the axial movement is used to push intermediate portions of the device into the walls of the curved portions of the vasculature rather than actually advancing the distal end forward. This lack of correspondence between the amount of axial push provided by the user at the proximal end and the resulting forward movement of the distal end makes navigation more difficult and less tactilely intuitive.

In addition, conventional catheter devices utilize multiple different materials to provide a gradient in bending stiffness from proximal end to distal end. However, whenever there is a transition between materials of differing stiffness, the bending, axial, and torsional stiffness profiles of the device includes an abrupt step change. Such abrupt changes in bending stiffness are undesirable because they can concentrate mechanical stresses at particular locations, cause kink points, disrupt the smooth movement and bending of the device, and complicate navigation in tortuous vasculature.

Accordingly, there exist several limitations in the field of catheter devices, and there is an ongoing need, for example, for devices that improve axial and/or torsional response, the distribution of bending forces, and/or are capable of providing a smooth bending stiffness profile.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Overview of Example Catheter Device

Figure 1:
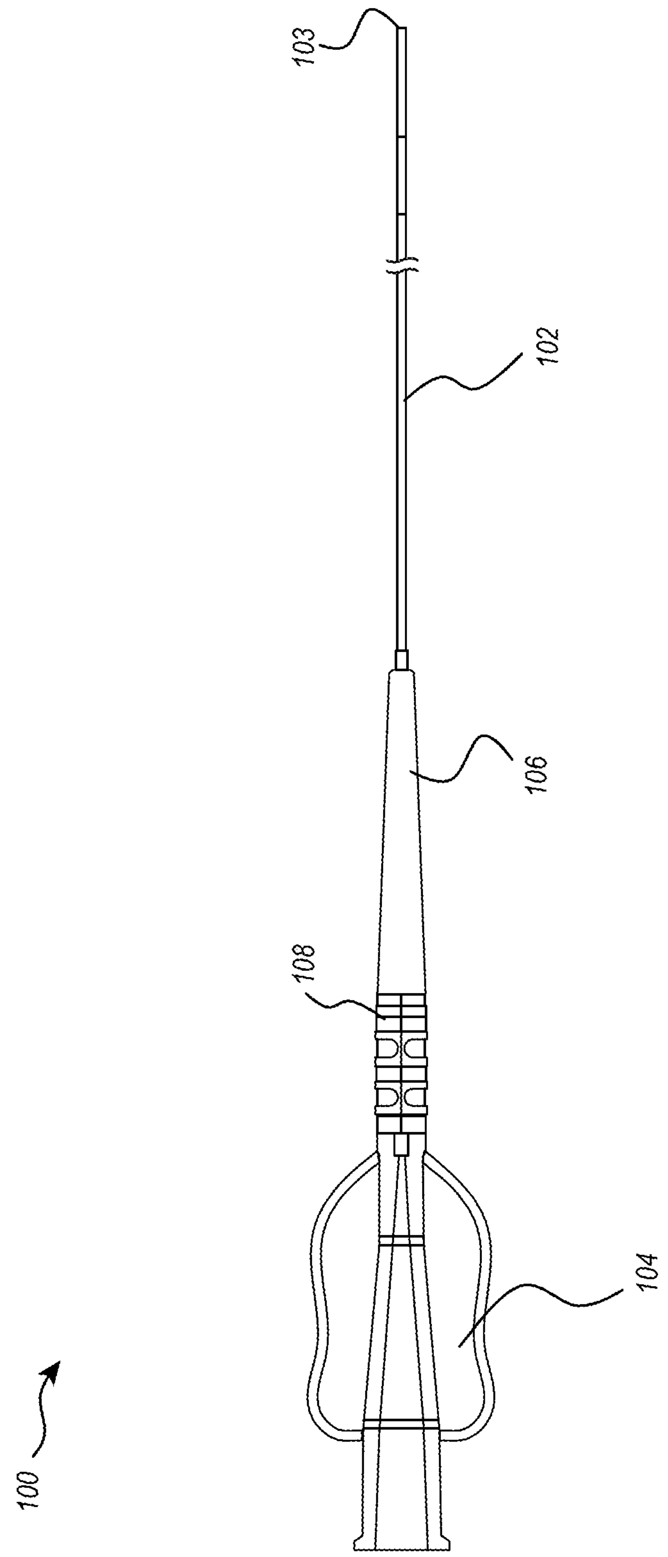
FIG. 1 illustrates an overview of a catheter system, including a catheter and hub.

FIG. 1 is an overview of an exemplary catheter device 100 that includes features, described in more detail below, that provide one or more of improved axial responsiveness, improved distribution of bending forces, and/or a smooth device bending stiffness profile.

The catheter device 100 includes a catheter 102 connected to a hub 104 at a proximal end and extending therefrom to a distal end 103. The catheter 102 may be coupled to the hub 104 using adhesive, a friction fit, through insertion molding, and/or other appropriate attachment means. A strain-relief member 106 is also disposed over the proximal section of the catheter 102 near the hub 104. The strain-relief member 106 has an outer diameter that substantially matches the adjacent section of the hub 104. The strain-relief member 106 extends for a distance from the hub 104 with a substantially constant outer diameter before tapering distally to the end where the catheter 102 emerges and extends farther distally. The strain-relief member 106 may include a groove pattern 108, disposed at the section of substantially constant outer diameter, that functions to provide additional flexibility to the strain-relief member 106 and/or to provide surface features for enhancing user grip and tactile engagement.

The working length of the catheter 102 (i.e., the distance between the distal end of the strain-relief (106) and the catheter (102) distal end (103) may vary according to particular application needs. As an example, the catheter 102 may have a working length of about 50 cm to about 200 cm, though shorter or longer lengths may be utilized where appropriate. The catheter size (typically referring to the inner diameter/lumen size) may also vary according to particular application needs. Examples include 0.010 inches, 0.013 inches, 0.017 inches, 0.021 inches, 0.027 inches, 0.030 inches, 0.035 inches, 0.038 inches, 0.045 inches, 0.065 inches, 0.085 inches, 0.100 inches, or a range including any two of the foregoing values as endpoints. The inside diameter of the catheter can taper from a smaller distal portion to a larger proximal portion. Smaller or larger sizes may be utilized in some applications as appropriate.

Although the distal section of the catheter 102 is shown in this example as having a straight shape, other embodiments may include a shaped distal tip. For example, the distal section of the catheter 102 may have an angled shape, a curved shape (e.g., 45 degree angle, 90 degree angle, J shape, etc.), a compound curved shape, or other appropriate angled or bent shape as known in the art.

The catheter device 100 described herein may be utilized for a variety of interventional applications, most commonly in cardiovascular, peripheral vascular, and neurovascular interventional procedures. Examples include accessing distal anatomy, crossing vessel lesions or blood clots, ischemic treatments, delivering therapeutic agents (e.g., embolic coils or other embolic agents), injecting diagnostic agents (e.g., contrast media or saline), retrieval applications, aspiration applications, or other applications where microcatheter use is beneficial.

Internal features of the catheter 102 are described in greater detail below. The outer surface of the catheter 102 may be coated with an appropriate coating material, such as a hydrophilic coating, to make the surface more lubricious. The coating material may cover substantially all of the working length of the catheter 102, or a portion thereof. For example, the coating material may be applied to the distal-most 30% to 80% of the working length of the catheter 102.

Figure 2:
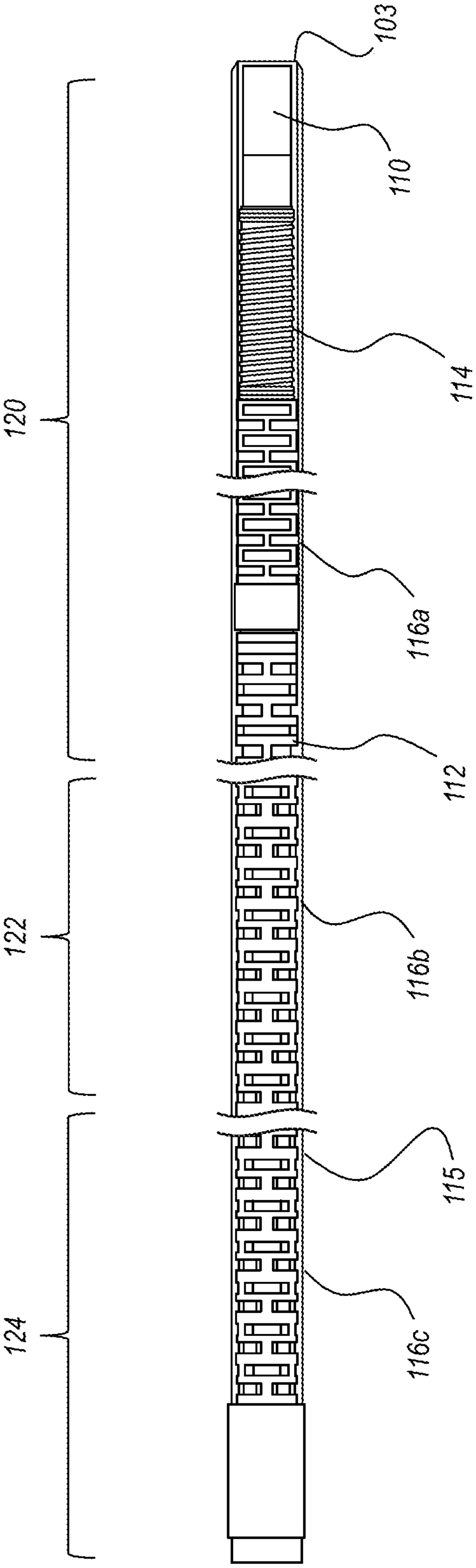
FIG. 2 illustrates a detailed view showing various sections of the catheter of the catheter system.

FIG. 2 illustrates a detailed view of the catheter 102, better showing some of the internal components and different longitudinal sections of the catheter 102. As shown, the catheter 102 includes an inner liner 110 that defines the inner lumen of the device. The liner 110 may be formed from polytetrafluoroethylene (PTFE) and/or other appropriate polymer. A coil 114 is positioned on the wire near the distal end 103. The coil 114 is attached to or positioned next to a microfabricated shaft 112 (also referred to herein as "inner shaft") that extends proximally therefrom. An outer member 115, formed from one or more polymer materials, is typically heat shrink laminated over and through the coil 114 and shaft 112, encasing both while also attaching to the liner.

In one embodiment, the coil 114 is formed from stainless steel and the shaft 112 is formed from nitinol. These materials, when used in combination with other features described herein, have been found to provide effective axial response, effective distribution of bending forces, and a smooth bending stiffness profile. Other embodiments may utilize one or more different materials for the coil 114, the shaft 112, or both. In some embodiments, for example, the shaft 112 may include other superelastic alloys and/or one or more polymers such as a polyether ether ketone (PEEK) or other polyaryl ether ketone (PAEK). In some embodiments, the coil 114 may include a superelastic alloy such as nitinol, one or more other metals, alloys, or polymers.

The catheter 102 is configured so that the overall bending stiffness profile transitions from higher stiffness (and less bending flexibility) at the proximal sections to lower stiffness (and greater bending flexibility) at the distal sections. In most applications, it is desirable to give the proximal sections of the device relatively high axial, torsional, and bending stiffness so they can provide good combination of flexibility, pushability, and torquability. Distal sections, however, are often navigated through tortuous vasculature and are thus preferably relatively more flexible in bending. This stiffness profile gradient can be created by adjusting certain features of the microfabricated shaft 112 and/or by utilizing different polymer materials to coat and embed the shaft 112 in the outer member 115. As explained in more detail below, in some embodiments, the microcatheter 112 and the outer member 115 are configured to work together to provide an overall stiffness profile that minimizes abrupt changes in stiffness and provides smooth stiffness transitions.

The illustrated embodiment includes a distal section 120, an intermediate section 122, and a proximal section 124. In the distal section 120, the outer member 115 is formed from a first polymer material 116*a*. In the intermediate section 122, the outer member 115 is formed from a second polymer material 116*b*. In the proximal section 124, the outer member 115 is formed from a third polymer material 116*c*. The polymer materials 116*a*, 116*b*, and 116*c* have different hardness and thus affect the stiffness of their respective sections differently. The second polymer material 116*b* has a higher hardness than the first polymer material 116*a*, and the third polymer material 116*c* has a higher hardness than the second polymer material 116*b*. Some embodiments may include more than three polymer materials. In such embodiments, as with the illustrated embodiment, the polymer materials may have progressively higher hardness moving from one polymer material to the next in the proximal direction.

As one example of a set of polymer materials found to be effective when utilized together, the first polymer material 116*a* may have a Shore D hardness of about 20 to about 30, the second polymer material 116*b* may have a Shore D hardness of about 30 to about 50, and the third polymer material 116*c* may have a Shore D hardness of about 50 to about 80. Other embodiments may vary these values as desired such as softer in the distal portion, but the foregoing values have been found to be particularly effective. The polymer materials 116*a*, 116*b*, and 116*c* may be formed from independently from appropriate polymers such as polyether block amide (PEBA) polymers and can range in polymer durometers from Shore A hardness of about 10 to Shore D hardness of about 100.

The shaft 112 also includes features that provide variable bending stiffness. As shown, the shaft 112 is a tube structure that includes a series of microfabricated cuts. The cuts form axially extending "beams" that connect successive circumferentially extending "rings". These cut patterns can be varied to adjust the bending stiffness of the shaft 112. For example, the bending stiffness can be attuned by adjusting the number of beams that reside between each pair of adjacent rings. A "two-beam section", such as shown in the distal section 120, includes two beams between each pair of adjacent rings. A "three-beam section", such as shown in the intermediate section 122 and proximal section 124, includes three beams between each pair of adjacent rings. All else being equal (shaft material, cut depth, cut width, cut spacing), a three-beam section has greater bending stiffness than a two-beam section. A "one-beam section" with a single beam connecting adjacent rings may also be utilized, and will have even less bending stiffness than a two-beam section, all else being equal. A "four-beam section" and/or section having greater than four beams may also be utilized, and will accordingly provide greater bending stiffness as the number of beams between each pair of adjacent rings is increased.

Figure 3A:
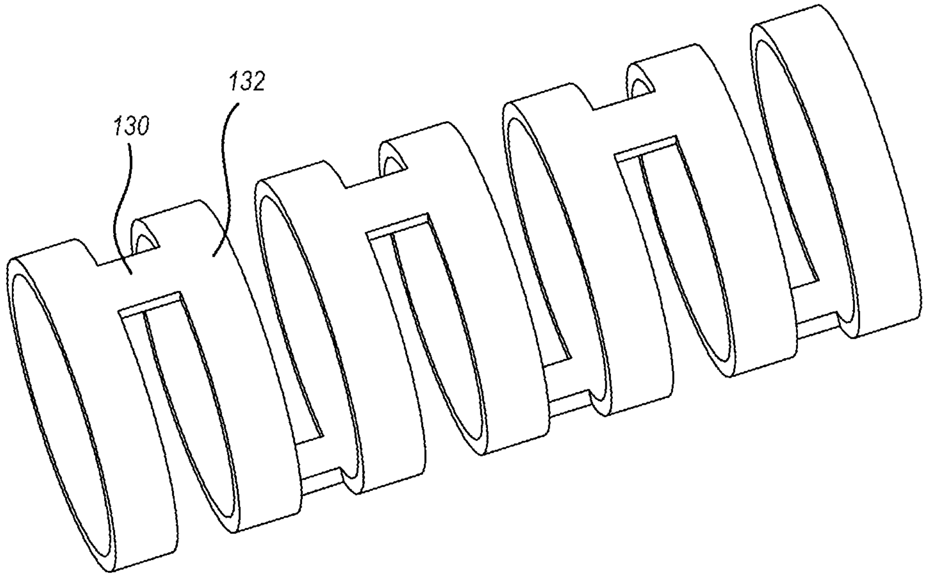
FIGS. 3A through 3C illustrate examples of a one-beam section, two-beam section, and three-beam section, respectively, that may be included in a microfabricated shaft used in the catheter system described herein.
Figure 3B:
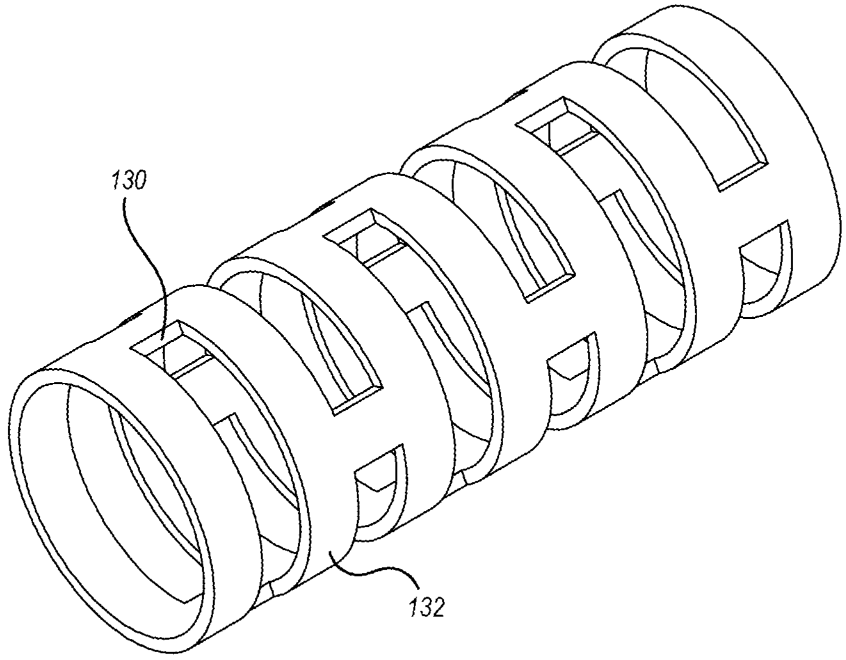
Figure 3C:
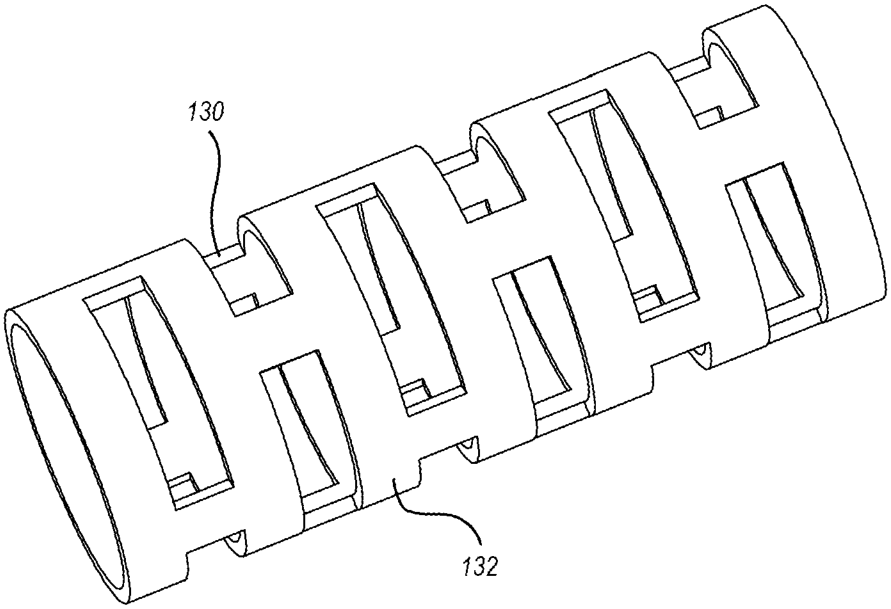

FIGS. 3A through 3C illustrate examples of a one-beam section, two-beam section, and three-beam section, respectively, showing exemplary arrangements of beams 130 and rings 132 in such sections. The beams can be configured in a variety of arrangements depending on the angular offset (or lack thereof) between successive sets of beams and/or how frequently the angular offset is applied (e.g., after each ring or after two or more rings). The one-beam section of FIG. 3A, for example, includes a 180 degree angular offset from one beam to the next, the two-beam section of FIG. 3B includes a 90 degree offset from one beam pair to the next, and the three-beam section of FIG. 3C includes a 120 degree angular offset from one set of beams to the next. While these types of offsets are beneficial, they are also associated with preferred bending planes, and other arrangements may be provided to minimize or eliminate preferred bending planes. Examples include a helical arrangement, a distributed arrangement, an imperfect ramp arrangement, and a sawtooth arrangement. Additional details regarding beam arrangements that may be utilized in the presently disclosed shaft 102 are provided in United States Patent Application No. 2020/0121308, which is incorporated herein by this reference in its entirety.

In addition to adjusting the number of beams disposed between rings, the bending flexibility of the shaft 112 may be controlled by adjusting the depth of cuts, the width of cuts, and/or the spacing of cuts. Typically, the width of cuts is set at a given value (e.g., corresponding to a cutting blade size), and it is easier to adjust cut depth and/or cut spacing during manufacture in order to provide the desired control over the bending stiffness profile. All else being equal, as ring width is reduced (i.e., cut spacing is reduced), cut width is increased, and/or beam width is reduced (i.e., cut depth is increased), the resulting bending stiffness is reduced. In the illustrated embodiment, the spacing between cuts in the three-beam section (which is coincident with the intermediate section 122 and proximal section 124) is progressively reduced as it gets closer to the distal section 120. Similarly, the two-beam section (which is coincident with the distal section 120) begins with larger spaces between cuts and progresses to less space between cuts as it gets closer to the coil 114 and the distal end 103. Preferably, transitions between different geometries (e.g., three-beam to two-beam) are configured so that bending stiffness is the same or similar across the transition of these sections. The shaft 112 thus provides a stiffness gradient by way of transitioning from a three-beam section to a two-beam section, and also within the respective sections by way of transitioning from cuts that are more spaced apart to cuts that are relatively less spaced apart.

At the distal end of the two-beam section, the cut pattern is configured with relatively high flexibility in order to provide a smooth transition to the high flexibility of the coil 114. In some embodiments, the coil 114 is omitted and replaced by more of the two-beam section (or alternatively, a one-beam section) that extends to a position at or near the distal end 103.

The lengths of the sections 120, 122, and 124 may be varied according to particular application needs or preferences. In one embodiment, the distal section 120 may have a length of about 5 cm to about 40 cm, and the intermediate section 122 may have a length of about 10 cm to about 50 cm, with the proximal section 124 taking up the remainder of the working length of the catheter 102. The illustrated embodiment shows that the shaft 112 transitions from a three-beam configuration to a two-beam configuration at the transition of the intermediate section 122 to the distal section 120. However, the transitions of the shaft 112 need not necessarily correspond to the transitions of polymer material that define the separate sections 120, 122, and 124. As explained in more detail below, the shaft 112 and outer member 115 are configured together to compensate for and minimize abrupt stiffness changes, and in some instances, this may involve shaft transition zones that do not overlap completely with polymer transitions of the outer member 115.

Figure 4:
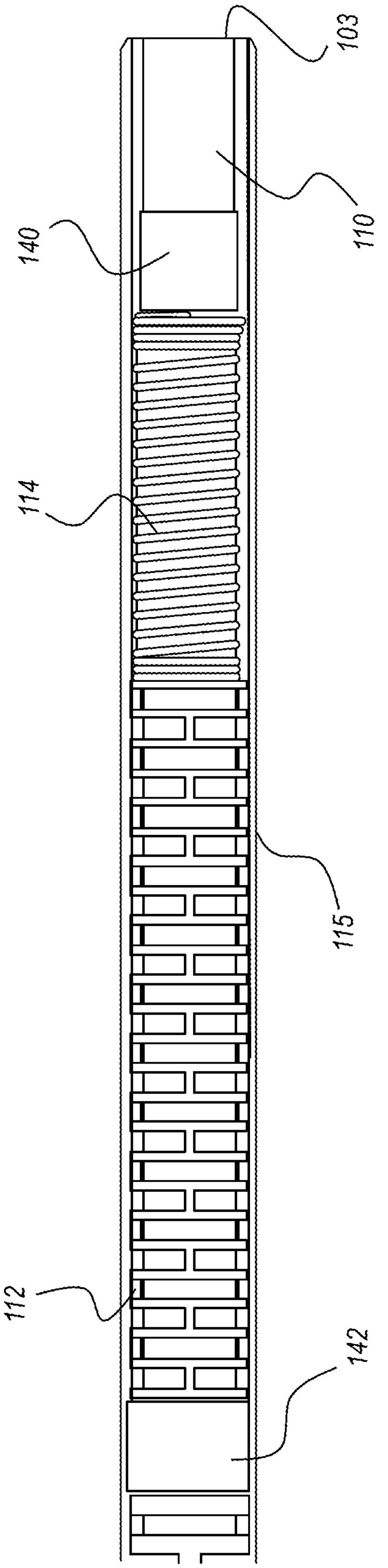
FIG. 4 illustrates a detailed view of a distal section of the catheter.

FIG. 4 illustrates a detailed view of the distal section 120 of the catheter 102, better showing certain distal features such as the liner 110, distal radiopaque marker band 140, coil 114, shaft 112, and proximal radiopaque marker band 142. The marker bands 140 and 142 are formed from a material more radiopaque than stainless steel. Examples include platinum, iridium, tungsten, other highly radiopaque metals, and alloys thereof. The distal marker band 140 provides an indication of the location of the distal end 103 of the catheter 102, whereas the proximal marker band 142 is offset by a predetermined length (e.g., 2 to 5 centimeters, or about 3 centimeters) to assist in proper positioning of detachable embolic coils or other components deployed through the catheter 102.

The shaft 112 may include a circumferential groove at the position where the proximal marker band 142 is placed. This groove can receive the marker band 142 such that the outer surface of the marker band 142 does not extend excessively beyond the outer diameter of the shaft 112. Once covered by the outer member 115, the outer diameter of the device over the proximal marker band 142 remains substantially flush.

In the illustrated embodiment, the coil 114 is variably pitched. Each end of the coil 114 includes a region of narrowed pitch that provides more improved transitions in bending stiffness from one geometry to another such as where the coil transitions to a microfabricated tube. As an example, the coil 114 may have a length of about 1 cm to about 3 cm. As shown, a portion of the liner 110 may extend a distance distally from the coil 114 and distal marker coil 140. This distance may vary from about 0.2 mm to about 2 mm, for example.

Bending Force Distribution

Figure 5A:
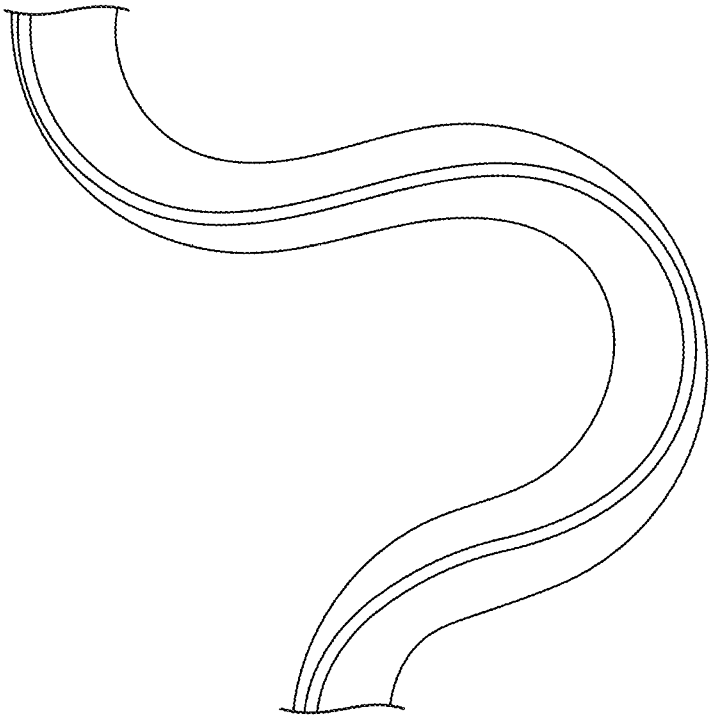
FIG. 5A (Prior Art)
FIGS. 5A through 5D are photographs illustrating differences in axial response that can occur within a vessel (artificial vessel shown), with FIGS. 5A and 5B showing the axial response of a conventional catheter and FIGS. 5C and 5D showing the improved axial response of a catheter according to the present disclosure.
Figure 5B:
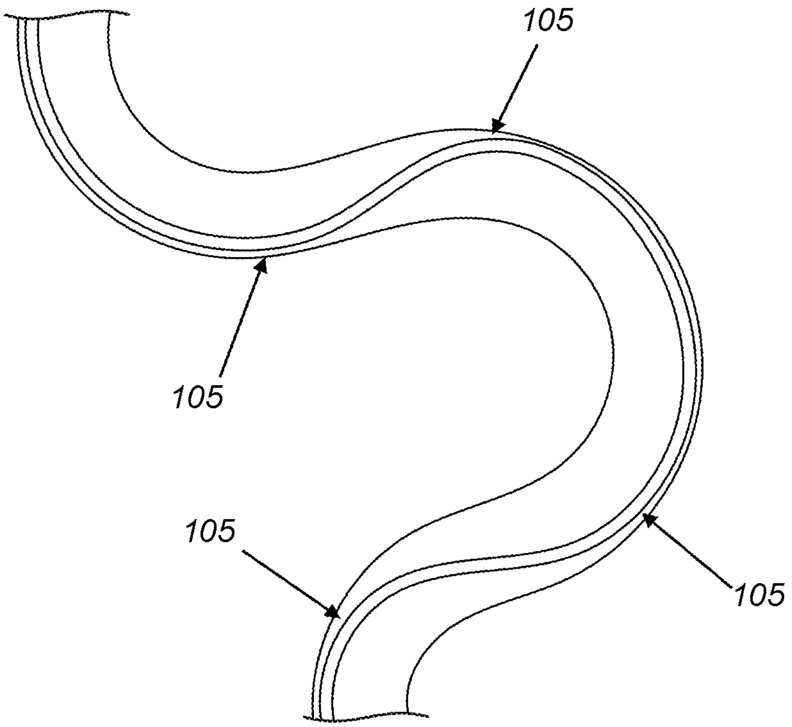
FIG. 5B (Prior Art)

The catheter devices described herein include features that effectively distribute bending forces and thereby provide improved axial response in use. FIGS. 5A and 5B illustrate a common limitation in navigating a conventional catheter (an Excelsior SL-10 shown in this example) through an artificial vasculature construct. As the catheter approaches a bend in a vessel, a certain length of the catheter extends around the bend (initial position in FIG. 5A). Upon further pushing, the initial axial movement is taken up in pushing the catheter against the walls of the vessel to fill the curves (after push position in FIG. 5B; see contact points

105 indicated in FIG. 5B) before any continued pushing results in actually advancing the distal tip of the catheter through the vasculature. This reduced correspondence between the amount of axial push provided by the user at the proximal end and the resulting forward movement of the distal end makes navigation more difficult and less tactilely intuitive.

In contrast to the response of conventional catheters as in FIGS. 5A and 5B, FIGS. 5C and 5D show navigation of the bend of the vessel using the catheter 102 as described herein. As shown, from the "initial" position (FIG. 5C) to the after-push position (FIG. 5D), less of the axial movement is taken up in filling the curve of the vessel, and more of the axial movement is thus transferred to actual movement of the distal end of the catheter 102. This function stems from the improved ability to distribute bending forces along the length of the catheter 102. By better distributing the bending forces, the catheter 102 better resists bending at any one particular location and can thereby better transfer proximal axial movement to the distal end of the device.

Figure 6:
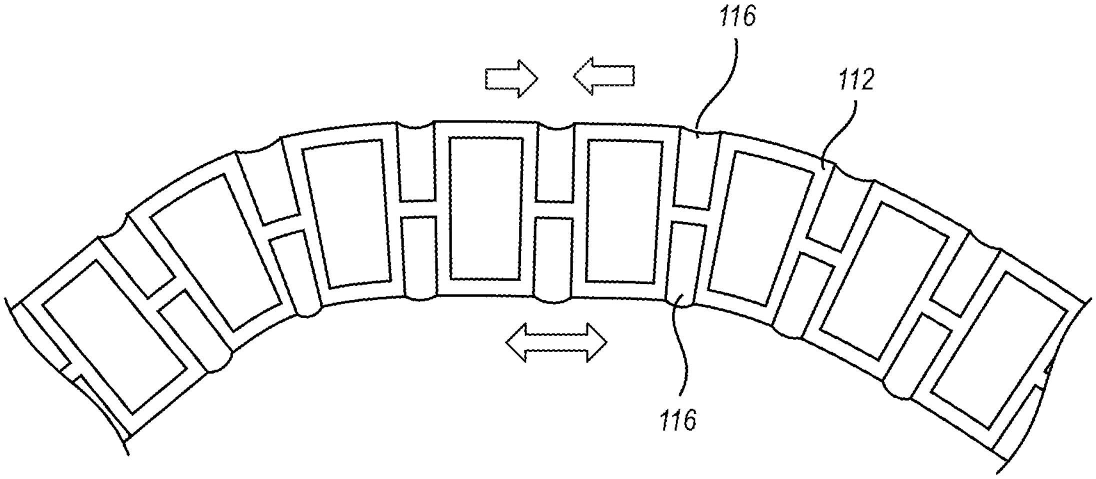
FIG. 6 schematically illustrates a section of the catheter during bending, showing how the catheter is configured to distribute bending, torsional, and axial forces in tortuous anatomy.

FIG. 6 further illustrates the ability of the catheter 102 to effectively distribute bending forces. FIG. 6 illustrates a portion of the shaft 112 during bending. The polymer material 116 fills the gaps between beams and rings of the shaft 112. For ease of viewing, the polymer material 116 is shown in discrete sections within each of the gaps of the shaft 112. In most cases, the polymer material 116 will fill the gaps, fuse with the liner 110, and also extend over the outer surface of the shaft 112 to fully encapsulate and embed the shaft 112.

During bending of the shaft 112, the shaft structure locally resists more bending stresses and distributes this stress to adjacent portions of the structure more effectively as compared to a coil or braid which are less likely to distribute bending stresses and more likely to kink. Additionally, the polymer material 116 effectively functions as a series of dampers each positioned between adjacent rings of the shaft 112. On the inner side of the bend, the polymer material 116 is compressed, and therefore provides a counteracting force that pushes outward against the rings and resists further bending. Similarly, on the outer side of the bend, the polymer material 116 is placed in tension, and therefore provides a counteracting force that pulls the rings inward and resists further bending. The bending stiffness of the catheter 102 is non-linear because it becomes increasingly resistant to bending, in a non-linear manner, as the bend angle is increased.

Figure 5C:
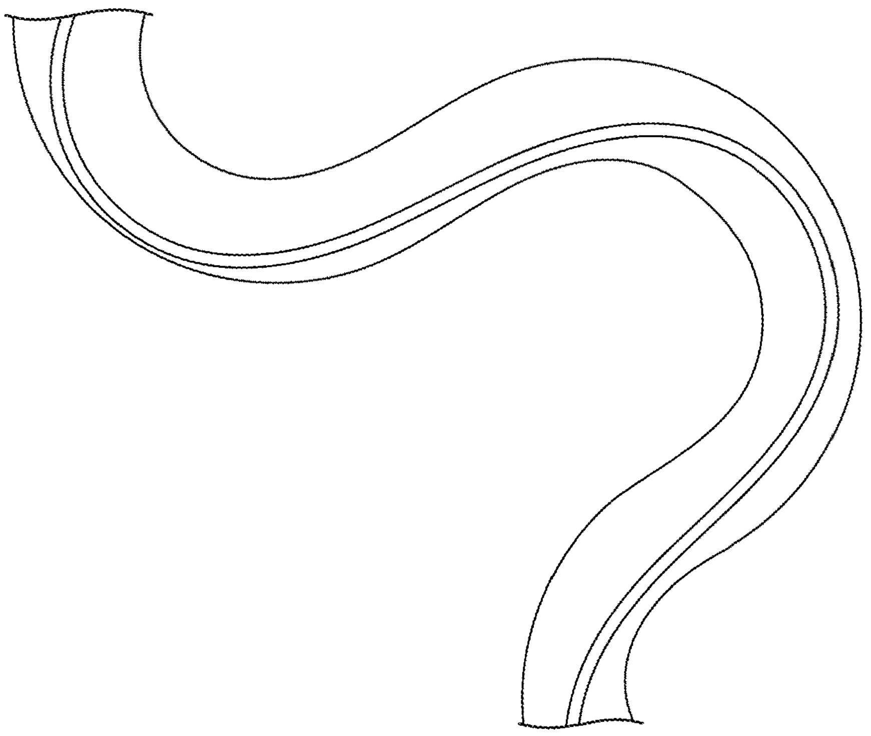
Figure 5D:
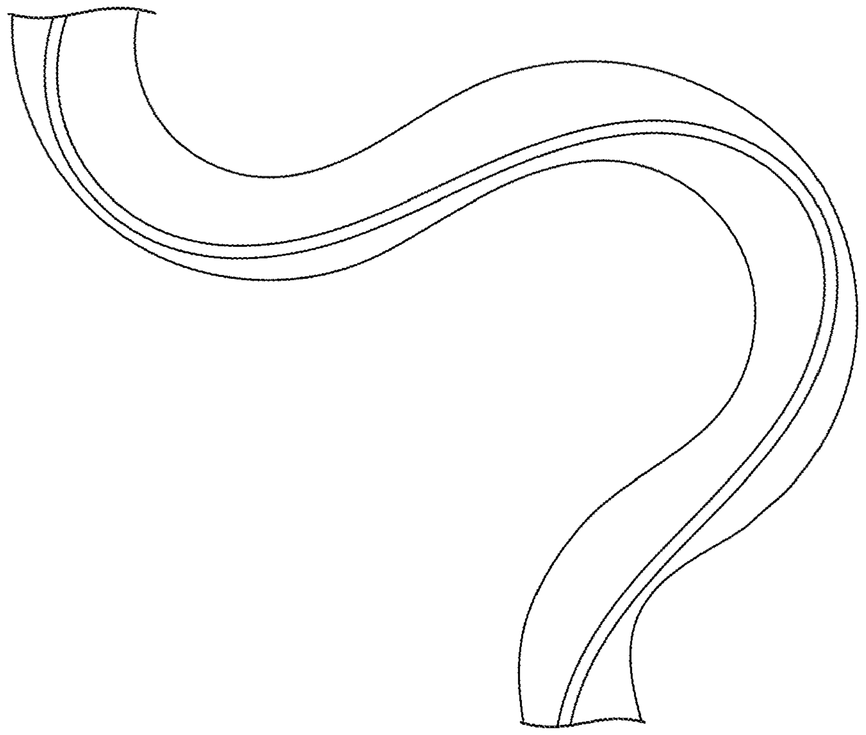

During bending, a conventional catheter will begin to bend at the apex and the cross-sectional shape of the catheter may tend to "ovalize". Once ovalization begins, resistance to bending decreases and it therefore becomes increasingly easier to bend with continued application of bending forces. In contrast, in the disclosed catheter 102, the bending resistance provided by the action of the microfabricated structure and polymer material 116 against the shaft 112 tends to distribute bending forces along the axial length of the catheter 102 and avoid ovalization and concentration of bending forces at a particular kink point. For example, the bending resistance will tend to spread a bend out to a larger radius of curvature rather than concentrating the bend at specific point thereby creating a kink location. The bending resistance provided by the catheter structure can therefore provide enhanced axial responsiveness (as illustrated by FIGS. 5C and 5D) and also enhanced protection against mechanical fatigue caused by bending stresses.

Smoothing of Bending Stiffness Profiles

Figure 7A:
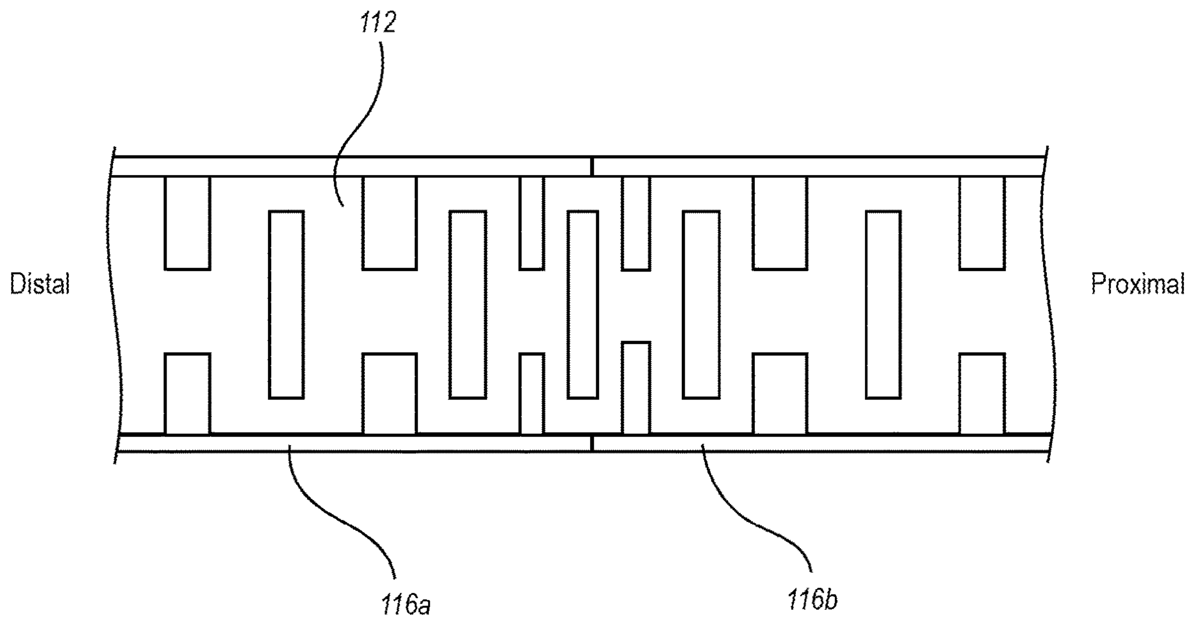
FIGS. 7A and 7B illustrate that the microfabricated shaft is configured to compensate for step changes in stiffness in the outer polymer layer due to transition from one polymer to another.
Figure 7B:
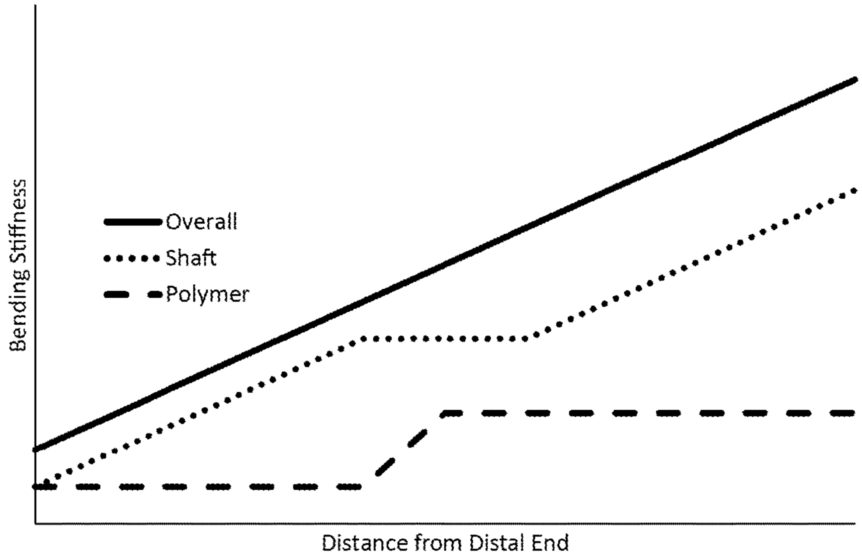

FIGS. 7A and 7B illustrate that the microfabricated shaft may be configured to compensate for step changes in stiffness in the outer member due to transition from one polymer to another. FIG. 7A illustrates a portion of the catheter 102 where the first polymer material **116*a* meets the second polymer material 116*b*. As shown in FIG. 7**B, this is associated with an abrupt step change in the bending stiffness of the polymer layer of the outer member. Such abrupt changes in bending stiffness are undesirable because they can concentrate mechanical stresses, cause kink points, disrupt the smooth movement and bending of the device, and complicate navigation in tortuous vasculature.

To compensate for this step change, the shaft is configured such that the bending stiffness changes complement and compensate for the abrupt change in bending stiffness of the polymer outer member. As a result, the overall bending stiffness of the catheter remains relatively smooth across the transition from the first polymer **116*a* to the second polymer 116*b*. Similar configurations can be utilized at other polymer transition zones to minimize and smooth out abrupt step changes in bending stiffness. The shaft 112 can be configured to compensate for the step change in a variety of ways. In the example of FIG. 7A, because the bending stiffness of the second polymer 116*b* is higher than the first polymer 116*a*, the configuration of the cuts/gaps of the shaft 112 remain constant or are narrowed for a short distance across the transition before spreading out again to generally increase shaft bending stiffness while moving further proximally. Other means of adjusting the bending stiffness of the shaft 112** as described herein (e.g., adjusting the number of beams and/or cut depth) may additionally or alternatively be used to achieve the result of smoothing the overall bending stiffness profile.

Configuring the shaft 112 to compensate for abrupt bending stiffness changes of the polymer outer member 115 beneficially avoids the complications of other conventional approaches to smoothing out such transitions. Prior approaches rely on complicated splicing arrangements or polymer co-extrusion and mixing techniques. These add layers of extra complication to the manufacturing process and may still only marginally resolve the abruptness of the transition. Other approaches utilize different diameters of polymer tubing and diameter gradients to compensate for transitions between polymer types. However, these approaches result in an uneven outer diameter or add the requirement to somehow manage this by overlaying even more material.

Figure 8A:
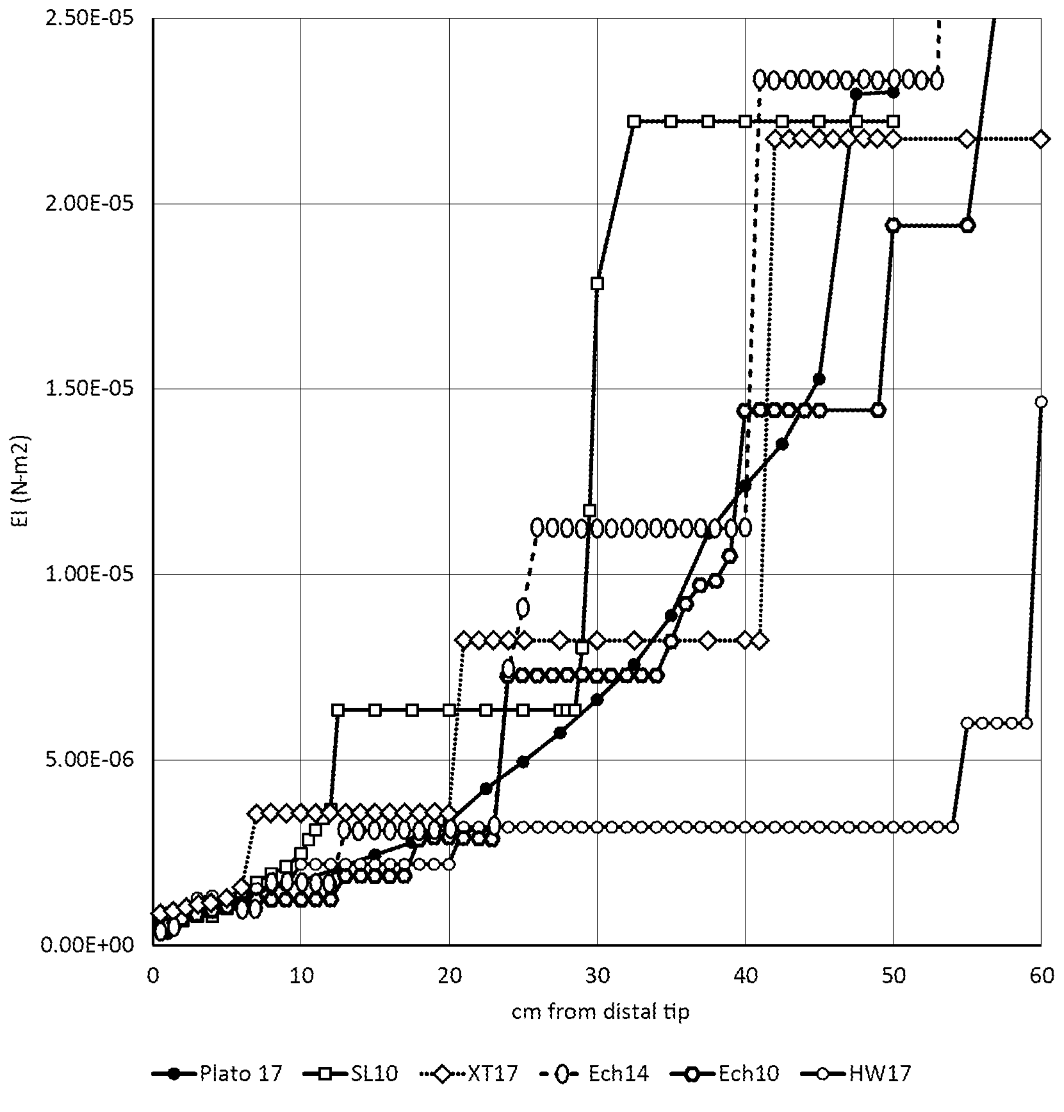
FIGS. 8A and 8B compare a bending stiffness profile of a catheter device according to the present disclosure (labelled "Plato 17") with bending stiffness profiles of various conventional catheter devices, with FIG. 8A showing bending stiffness up to 60 cm from the distal tip and FIG. 8B showing bending stiffness up to 15 cm from the distal tip.
Figure 8B:
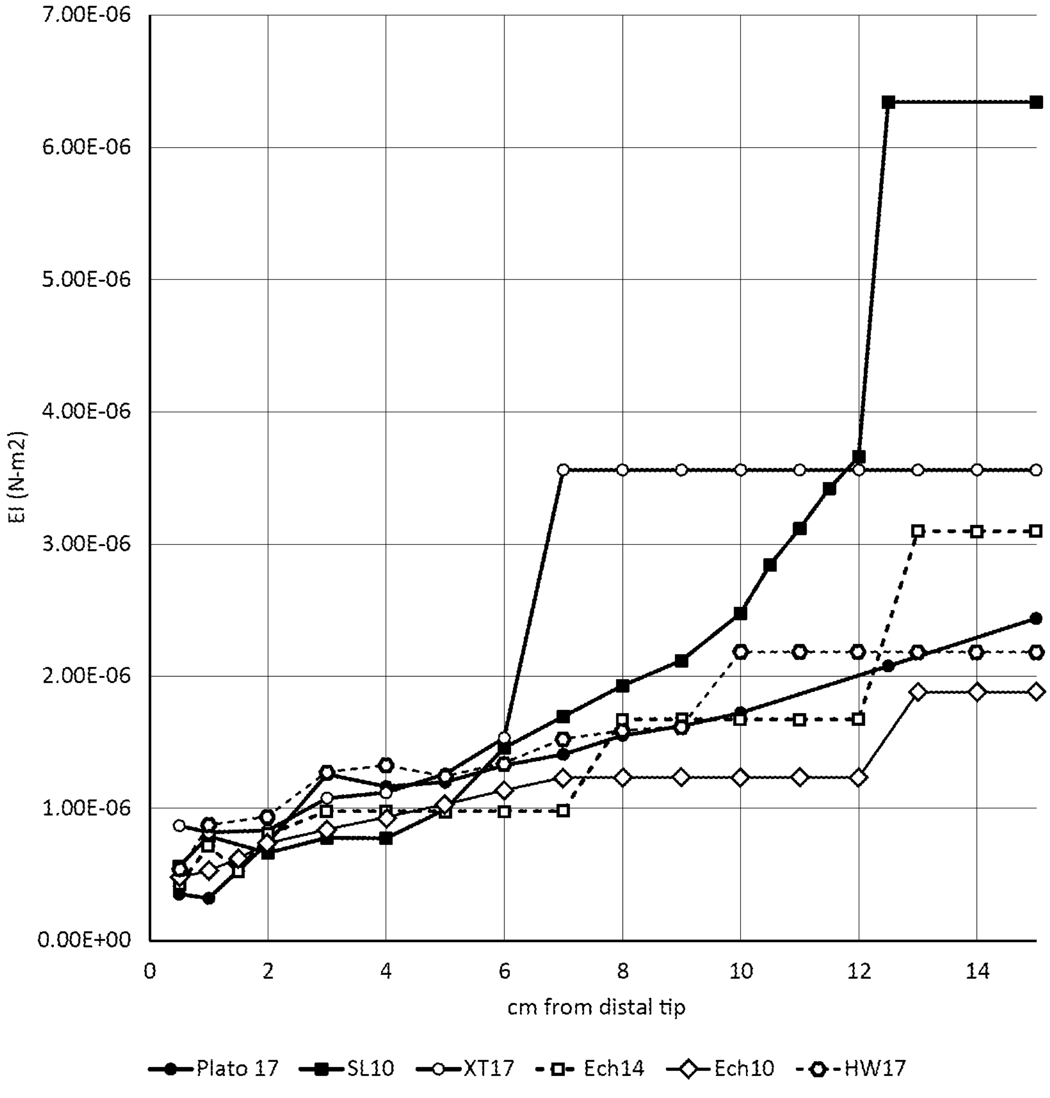

The smoothing features described herein enable the manufacture of microcatheters having improved bending stiffness profiles as compared to conventional microcatheters. FIGS. 8A and 8B illustrate the results of testing comparing the bending stiffness profile of a catheter made according to the present disclosure (labelled "Plato 17") to the bending stiffness profiles of several conventional microcatheters. In the Figures, "SL10" refers to an Excelsior SL-10 (sold by Stryker Neurovascular), "XT17" refers to an Excelsior XT-17 (sold by Stryker Neurovascular), "Ech14" refers to an Echelon 14 (sold by Medtronic), "Ech10" refers to an Echelon 10 (sold by Medtronic), and "HW17" refers to a Headway 17 (sold by MicroVention Terumo). FIG. 8A illustrates bending stiffness profiles over the distal 50 to 60 cm of the devices, FIG. 8B provides a closer view of the bending stiffness profiles over the distal 15 cm of the devices. In the Figures, the Plato 17 data represents an average of 5 replicates, the SL10 data represents an average of 3 replicates, the XT17 represents an average of 2 replicates, the Ech14 represents an average of 2 replicates, the Ech10 represents an average of 3 replicates, and the HW17 represents an average of 2 replicates. As shown, the catheter corresponding to the present disclosure provides a smoother profile with less abrupt changes in bending stiffness.

Table 1 presents the data of FIGS. 8A and 8B by listing different distal section sizes and providing the highest measured "slope" within that section. The "slope" represents the change in bending stiffness ($N \cdot m^2$) over the distance between measured data points (cm). As evident from the data points in FIGS. 8A and 8B, note that measurements were taken at increments of 0.5 cm to 2.5 cm, usually every 1 cm with smaller increments at regions where a clear polymer transition was evident and larger increments once reaching about 15 to 20 cm from the distal end. The slope therefore provides an indication of the abruptness of bending stiffness changes across the given section of the catheter.

TABLE 1

Stiffness Changes of Various Microcatheters Across Different Distal Section Sizes.

| Section Measured from Distal End (cm) | Highest Measured "Slope" Within Section ((N · m²)/cm) |
|---|---|
| **Plato 17** | |
| 0-15 | $5.20e^{-7}$ |
| 0-35 | $5.20e^{-7}$ |
| 0-50 | $8.91e^{-7}$ |
| **SL-10** | |
| 0-15 | $5.37e^{-6}$ |
| 0-35 | $1.22e^{-5}$ |
| 0-50 | $1.22e^{-5}$ |
| **XT-17** | |
| 0-15 | $2.03e^{-6}$ |
| 0-35 | $4.65e^{-6}$ |
| 0-50 | $1.35e^{-5}$ |
| **Echelon-14** | |
| 0-15 | $1.42e^{-6}$ |
| 0-35 | $4.32e^{-6}$ |
| 0-50 | $1.21e^{-5}$ |
| **Echelon-10** | |
| 0-15 | $6.46e^{-7}$ |
| 0-35 | $4.39e^{-6}$ |
| 0-50 | $4.97e^{-6}$ |
| **Headway-17** | |
| 0-15 | $7.05e^{-7}$ |
| 0-35 | $1.00e^{-6}$ |
| 0-50 | $1.00e^{-6}$ |

As shown, the Plato 17 has the lowest measured slope across the distal 15 cm section, across the distal 35 cm section, and across the distal 50 cm section. Based on the data of FIGS. 8A and 8B, as further disclosed in Table 1, in some embodiments a catheter device as described herein has a bending stiffness slope ($(N \cdot m^2)/cm$)) of no more than about $6.0\times10^{-7}$ for a distal 15 cm section, no more than about $9.0\times10^{-7}$ for a distal 35 cm section, and/or no more than about $9.0\times10^{-7}$ for a distal 50 cm section. While the Plato 17 device configured according to the present disclosure achieved each of the foregoing features, none of the other prior catheter devices tested were able to do so.

In some embodiments, at least a portion of the distal 35 cm of the catheter device has a bending stiffness of $5\times10^{-6}$ $N \cdot m^2$ or greater. In some embodiments, in addition to the foregoing stiffness minimum, a catheter device as described herein has a bending stiffness slope ($(N \cdot m^2)/cm$)) of no more than about $4.0\times10^{-6}$ for a distal 35 cm section and/or no more than about $4.5\times10^{-6}$ for a distal 50 cm section. As shown in FIGS. 8A and 8B and Table 1, while the Plato 17 device meets these requirements, the Headway-17 catheter does not meet the minimum bending stiffness requirement, and none of the other tested catheters meet the slope requirements.

Figure 9:
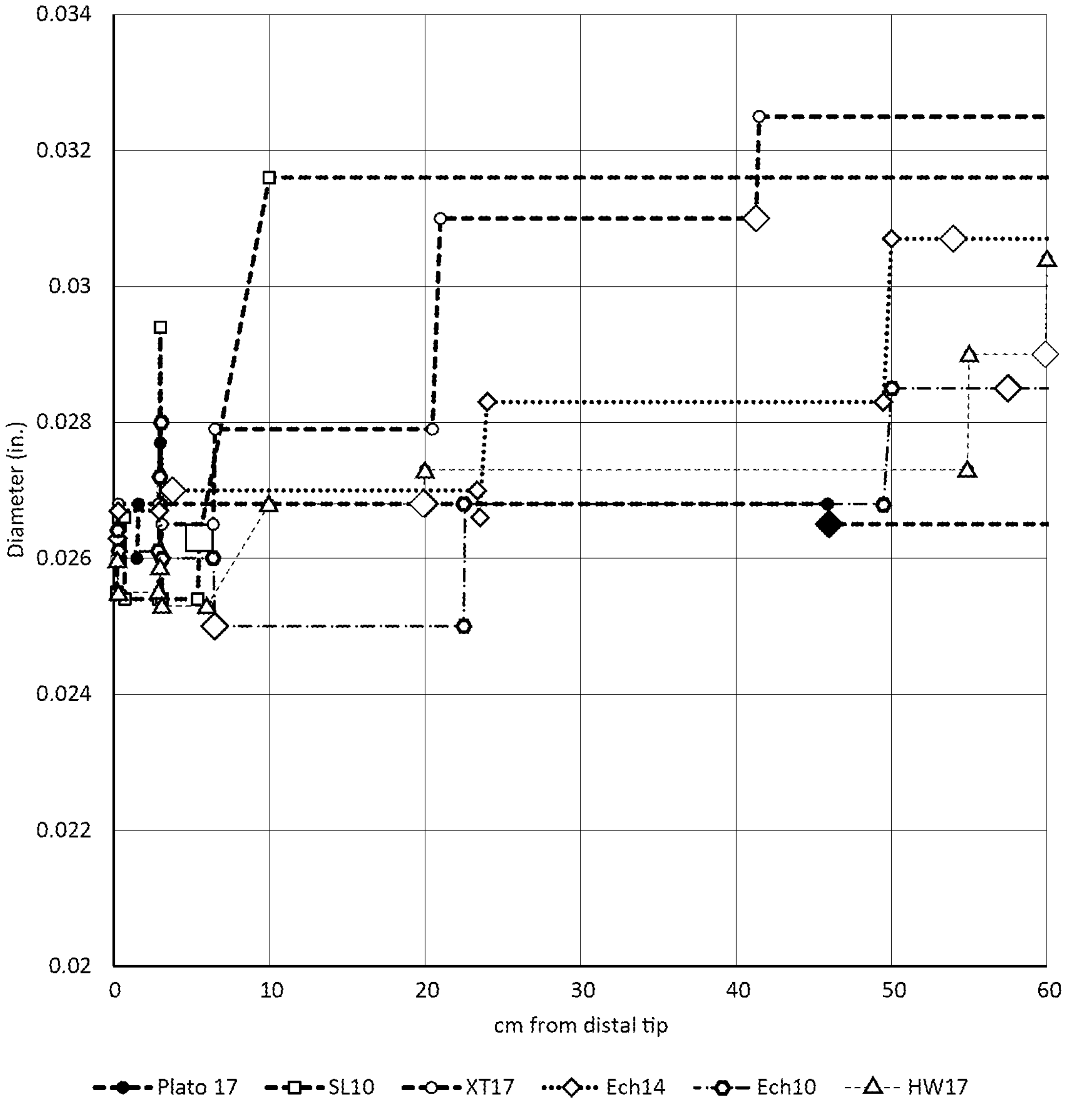
FIG. 9 compares outer diameters along distal lengths of a catheter device according to the present disclosure (labelled "Plato 17") to various conventional catheter devices.

FIG. 9 compares outer diameters along distal lengths of the Plato 17 device according to the present disclosure to various conventional catheter devices. The larger data points represent points where a polymer transition is visibly apparent. The data from FIG. 9 is also represented in Table 2, which shows the maximum diameter change within the distal 15 cm section and the distal 35 cm section of each of the catheter devices. As shown, the Plato 17 diameter changes by no more than 0.0017 inches across the distal 15 cm section and across the distal 35 cm section.

TABLE 2

Diameter Changes of Various Microcatheters Across Different Distal Section Sizes.

| Section Measured from Distal End (cm) | Maximum Diameter Change (inches) |
|---|---|
| **Plato 17** | |
| 0-15 | .0017 |
| 0-35 | .0017 |
| **SL-10** | |
| 0-15 | .0062 |
| 0-35 | .0062 |
| **XT-17** | |
| 0-15 | .0024 |
| 0-35 | .0055 |
| **Echelon-14** | |
| 0-15 | .0017 |
| 0-35 | .0020 |
| **Echelon-10** | |
| 0-15 | .0022 |
| 0-35 | .0022 |
| **Headway-17** | |
| 0-15 | .0015 |
| 0-35 | .0020 |

In some embodiments, a catheter device as described herein has (1) a bending stiffness of $5\times10^{-6}$ $N \cdot m^2$ or greater in at least a portion of the distal 35 cm of the catheter device, (2) a change in outer diameter of no more than 0.002 inches across the distal 15 cm and/or distal 35 cm section, and (3) a bending stiffness slope ($(N \cdot m^2)/cm$)) of no more than about $1.3\times10^{6}$ for a distal 15 cm section, no more than about $4.2\times10^{-6}$ for a distal 35 cm section, and/or no more than about $1.1\times10^{-5}$ for a distal 50 cm section. While the Plato 17 device configured according to the present disclosure achieved each of the foregoing features, none of the other prior catheter devices tested were able to do so. That is, the Headway-17 catheter does not meet the minimum bending stiffness requirement, the Echelon-10 does meet the diameter change requirement, and none of the other tested catheters meet the slope requirements.

In some embodiments, the beneficial bending stiffness profile features described above are specifically applicable to a transition section where a first polymer of the outer member transitions to a second polymer of the outer member.

In some embodiments, the shaft 112 maintains substantially the same wall thickness along its length. Other catheter devices based on coils and/or braids will most often have adjusted wall thicknesses at transition points. Changes in wall thickness can introduce additional kink or stress points and/or require additional manufacturing steps to manage.

In some embodiments, there may be an acceptable bending stiffness change associated with the distal tip region because the shaft 112 transitions to the coil 114 and/or the coil 114 transitions to the distal-most section of liner 110. These stiffness changes may be acceptable because they are so near the distal end 103. Thus, in some embodiments, the distal-most 3 to 5 cm may be excepted from the foregoing bending stiffness change limits.

Fatigue Resistance

The catheter devices described herein also beneficially provide effective fatigue resistance. For example, in a bend and twist fatigue test method based on ASTM E2948, catheter devices as described herein are capable of achieving greater than 20 cycles before breaking. The bend and twist fatigue test method is described in more detail in document TM-00127, which is attached hereto as Appendix 1. In short, the test is adapted from ASTM E2948, which is a standard test method for measuring rotating bending fatigue of solid round fine wire.

The effective fatigue resistance of the disclosed catheter devices may be present along the entire length of the shaft portion of the device, or along one or more sub-sections of the device (e.g., along one or more sections having length of about 3 to 35 cm, or about 3 to 20 cm, or about 3 to 10 cm). The effective fatigue resistance is provided by one or more of the following parameters: (1) maintaining ring widths at less than or equal to about 30% of the corresponding outer diameter of the shaft 112; and/or (2) maintaining cut depths at greater than or equal to about 11% of the outer diameter of the shaft 112.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

As used herein, the term "microfabricated" refers to any fabrication process capable of manipulating a stock material to form a catheter device having one or more of the features disclosed herein, including any fabrication process capable of forming gaps in an inner shaft as disclosed herein. Examples include, but are not limited to, laser cutting and blade cutting.

For any given element of component of a described embodiment, any of the possible alternatives listed for that element or component may generally be used individually or in combination with one another, unless implicitly or explicitly stated otherwise.

Unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A catheter device, comprising:

an inner shaft comprising a plurality of gaps formed therein; and an outer member comprising a polymer material disposed within the gaps and comprising a transition section where a first polymer transitions to a second polymer of different hardness, wherein the outer shaft includes a change in bending stiffness at the transition section due to the transition from the first polymer to the second polymer, and wherein the size and/or spacing of the plurality of gaps of the inner shaft at the transition section are configured such that the bending stiffness of the inner shaft at the transition section compensates for the change in bending stiffness of the outer member at the transition section.

2. The catheter device of claim 1, wherein the inner shaft includes a plurality of axially extending beams that couple a plurality of circumferentially extending rings.

3. The catheter device of claim 2, wherein the inner shaft includes one or both of a three-beam section and a two-beam section, wherein the three-beam section is disposed proximal of the two-beam section, and wherein at least a portion of the three-beam section has a higher bending stiffness than the two-beam section.

4. The catheter device of claim 2, wherein the axially extending beams extend parallel to a longitudinal axis of the tube structure.

5. The catheter device of claim 2, wherein the circumferentially extending rings form fully enclosed rings.

6. The catheter device of claim 1, wherein the second polymer is proximal of the first polymer and has a greater hardness than the first polymer such that the outer member increases in bending stiffness across the transition section in the distal to proximal direction.

7. The catheter device of claim 1, further comprising an inner liner around which the shaft is positioned.

8. The catheter device of claim 7, wherein the polymer material of the outer member is fused to the liner, fills the gaps of the shaft, and covers outer surfaces of the shaft to encapsulate and embed the shaft.

9. The catheter device of claim 1, wherein the shaft is formed from nitinol.

10. The catheter device of claim 1, wherein the outer material comprises one or more polyether block amide polymers.

11. The catheter device of claim 1, wherein the catheter device has a bending stiffness slope ((N·m$^2$)/cm)) of no more than about $6.0\times10^{-7}$ for a distal 15 cm section, no more than about $9.0\times10^{-7}$ for a distal 35 cm section, and/or no more than about $9.0\times10^{-7}$ for a distal 50 cm section.

12. The catheter device of claim 1, wherein at least a portion of the distal 35 cm of the catheter device has a bending stiffness of $5\times10^{-6}$ N·m$^2$ or greater, and wherein the catheter device has a bending stiffness slope ((N·m$^2$)/cm)) of no more than about $4.0\times10^{-6}$ for a distal 35 cm section and/or no more than about $4.5\times10^{-6}$ for a distal 50 cm section.

13. The catheter device of claim 1, wherein: (1) at least a portion of the distal 35 cm of the catheter device has a bending stiffness of $5\times10^{-6}$ N·m$^2$ or greater; (2) the catheter device has a change in outer diameter of no more than 0.002 inches across the distal 15 cm and/or distal 35 cm section; and (3) the catheter device has a bending stiffness slope ((N·m$^2$)/cm)) of no more than about $1.3\times10^{-6}$ for a distal 15 cm section, no more than about $4.2\times10^{-6}$ for a distal 35 cm section, and/or no more than about $1.1\times10^{-5}$ for a distal 50 cm section.

14. The catheter device of claim 1, further comprising a coil disposed distal of the shaft.

15. The catheter device of claim 14, wherein the coil has a variable pitch.

16. A catheter device, comprising:

a microfabricated inner shaft having a plurality of gaps formed therein, wherein the inner shaft includes a plurality of axially extending beams that couple a plurality of circumferentially extending rings, wherein the inner shaft includes a three-beam section and a two-beam section, wherein the three-beam section is disposed proximal of the two-beam section, and wherein at least a portion of the three-beam section has a higher bending stiffness than the two-beam section; and an outer member comprising a polymer material disposed within the gaps, wherein the outer member includes multiple different polymer durometers, and wherein the outer member includes a transition section where a first polymer transitions to a second polymer of different hardness, wherein the outer member includes a change in bending stiffness at the transition section due to the transition from the first polymer to the second polymer, wherein the size and/or spacing of the plurality of gaps of the inner shaft at the transition section are configured such that the bending stiffness of the inner shaft at the transition section compensates for the change in bending stiffness of the outer member at the transition section.

17. The catheter device of claim 16, wherein the second polymer proximal of the first polymer and has a greater hardness than the first polymer such that the outer member increases in bending stiffness across the transition section in the distal to proximal direction, and wherein the shaft does not increase in bending stiffness across at least a portion of the transition section in the distal to proximal direction to compensate for the increase in bending stiffness of the outer member.

18. The catheter device of claim 16, wherein the axially extending beams extend parallel to a longitudinal axis of the tube structure.

19. The catheter device of claim 16, wherein the circumferentially extending rings form fully enclosed rings.

* * * * *